(12) United States Patent
Shinohara et al.

(10) Patent No.: US 6,750,052 B1
(45) Date of Patent: Jun. 15, 2004

(54) LENS EPITHELIAL CELL DERIVED GROWTH FACTOR

(75) Inventors: Toshimichi Shinohara, Chestnut Hill, MA (US); Dhirendra Singh, Brookline, MA (US); Leo T. Chylack, Jr., Duxbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/121,211

(22) Filed: Jul. 23, 1998

Related U.S. Application Data

(60) Provisional application No. 60/053,549, filed on Jul. 23, 1997.

(51) Int. Cl.$^7$ .............................. C12N 1/21; C12N 5/10; C12N 15/63; C12N 21/04
(52) U.S. Cl. ................................ 435/252.3; 435/320.1; 435/325; 435/810; 536/23.5; 536/24.1
(58) Field of Search .............................. 435/325, 252.3, 435/320.1; 536/23.8, 24.3, 24.1

(56) References Cited

U.S. PATENT DOCUMENTS 5,604,293 A * 2/1997 Fiddes et al. ............... 530/399

FOREIGN PATENT DOCUMENTS

| WO | WO 96/09054 | 3/1986 |
| WO | WO 92/19727 | 11/1992 |
| WO | WO 94/01124 | 1/1994 |
| WO | WO 95/09004 | 4/1995 |

OTHER PUBLICATIONS

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, p. 9.50.*

Database Medline on STN, Medline Accession No. 1999366075, US National Library of Medicine, Bethesda, MD, USA, Li et al. Promotive effects of basic fibroblast growth factor on proliferation of bovine lens epithelial cells. Chung–hua Yen Ko Tsa Chih Chi, Mar. 1997.*

Ngo et al., in The Protein Folding Problem and Tertiary Structure Prediction, Merz and Le Grand (Eds), Aug. 1994, Springer Verlag, pp. 433 and 492–495, Nov. 1989.*

International Search Report for PCT/US98/09801.

Ochs, R. L., et al., File: EHUM2 Database Accesion No. U94319, "Autoantibodies in Atopic Dermatitis and Interstitial Cystitis: Characterization of the Major Autoantibody/Autoantigen System" (Apr. 22, 1997).

Singh, E.P. et al., File: EMBL Database Accesion No. AF063020, "Lens Epithelium–Derived Growth Factor (LEDGF)" (Jul. 2, 1998).

Nakamura H., et al., "Molecular Cloning of Complementary DNA for a Novel Human Hepatoma–Derived Growth Factor. Its Homology with High Mobility Group–1 Protein.", *J. Biol. Chem.*, 269:40, Oct. 7, ppg. 25143–25149 (1994).

Izumoto, Y. et al., "Hepatoma–Derived Growth Factor Belongs to a Gene Family in Mice Showing Significant Homology in the Amino Terminus", *Biochem. and Biophys. Res. Commun.*, 238, ppg. 26–32, Article No. RC977233 (1997).

Alterio, J. et al., "Characteriztion of a Bovine Acidic FGF cDNA Clone and its Expression in Brain and Retina", *FEBS LTRS*, 242, 1, ppg. 41–46 (Dec. 1988).

* cited by examiner

*Primary Examiner*—David S. Romeo
(74) *Attorney, Agent, or Firm*—Wolf, Greenfield & Sacks, P.C.

(57) ABSTRACT

The invention pertains to nucleic acids encoding a lens epithelial cell derived growth factor protein, including fragments and biologically functional variants thereof. The invention also pertains to therapeutics and diagnostics involving the foregoing proteins and genes and agents that bind the foregoing proteins and genes.

8 Claims, 4 Drawing Sheets

A

B

LENS EPITHELIAL CELL DERIVED GROWTH FACTOR

GOVERNMENT SUPPORT

This invention was made in part with government support under National Institutes of Health (NIH) RO1 project grant numbers EY-00484, EY-05230, EY-10958 and EY-10824. Accordingly, the United Stated government may have certain rights in this invention.

RELATED APPLICATIONS

This application claims priority under 35 USC § 119(e) from U.S. Provisional Patent Application Serial No. 60/053,549 filed on Jul. 23, 1997, entitled LENS EPITHELIAL CELL DERIVED GROWTH FACTOR. The content of the provisional application is hereby expressly incorporated by reference.

FIELD OF THE INVENTION

This invention relates to nucleic acids and encoded polypeptides of a lens epithelial cell derived growth factor (LEDGF), and diagnostics and therapeutics related to medical conditions associated with such genes and polypeptides, including cataracts.

BACKGROUND OF THE INVENTION

The term cataract is used to define the opacification of the normally clear and transparent crystalline lens. Several types of cataract etiology have been described. For example, congenital cataracts occur as a complication of intrauterine rubella, herpes simplex, herpes zoster, syphilis and cytomegalic inclusion disease, the majority being idiopathic or inherited. Acquired cataracts result from trauma, radiation, drugs, metabolic disorders, ocular inflammatory disorders, or aging (senile or age-related cataracts). It has been estimated that nearly one billion elderly people throughout the world have age-related cataracts [ARCs] (Thylefors et al., *Available Data on Blindness*, Geneva, Switzerland; WHO Program for the Prevention of Blindness, 1994). The underlying mechanisms responsible for ARCs, however, are not well understood.

Although the anterior lens is covered with a single layer of cuboidal lens epithelial cells (LECs), most of the remaining lens is composed of anucleated fiber cells. With age, even though the lens enlarges, the epithelial cell density and cytological activity decline (Guggenmoos-Holzmann et al., *Invest. Ophthalmol. Vis. Sci.* 30:330–332, 1989, Konofsky et al., *Ophthalmology* 94:875–880, 1987, and Straatsma et al., *Am. J. Ophthalmol.* 112:283–296 1991); this decrease is most pronounced in lenses with cortical and mixed cataracts. Also in these cataracts, there is greater LEC metaplasia than in the normal lens (Saitoh et al., *Nippon Ganka Gakkai Zasshi* 94:176–180, 1990, Streeten and Eshaghian, *Arch. Ophthalmol.* 96:1653–1658, 1978, and von Sallmann, *Am. J. Ophthalmol.* 44:159–170, 1957). Since the LECs maintain lens homeostasis, a decrease in epithelial cell number or metabolic activity is expected to disturb normal lens physiology.

For survival, the cells require growth or proliferation factors, and several such factors have been reported: neurotrophic factor for neurons (Cowan et al., *Science* 225:1258–1264, 1984, Purves, *Body and brain. A trophic theory of natural connections*. Harvard University Press. Cambridge, Mass. pp. 231, 1988, Barde, *Neuron* 2:1525–1534, 1989, and Oppenheim, *Science* 240:919–922, 1991), colony stimulation factor for myeloid cells (Metcalf, *Nature* 339:27–30, 1989, Williams et al., *Nature* 343:76–78, 1990, and Koury and Bondurant, *Science* 248:378–381, 1990), specific hormones for endocrine-dependent cells (Kerr and Searle, *Virchows. Arch. B. Cell Pathol.* 13:87–92, 1973, Krypaniou and Issacs, *Endocrinology* 122:552–562, 1988, and Wyllie et al., *J. Pathol.* 111:85–94, 1973), and specific growth factors for oligodendrocytes (Barres et al., *Cell* 70:31–46, 1992). Ishizaki et al. predicted that LECs must have such growth factors (*J. Cell Biol.* 121:899–908, 1993].

It was demonstrated recently (Ibaraki et al., *Exp. Eye Res.* 64:229–238, 1997 and Singh et al., *J. Immunol.* 155:993–999, 1995), that auto-antibodies against lens P-crystallins induced LEC damage and cataract formation in mice. Both serum and monoclonal antibody (Ab) transfer studies established that humoral rather than cellular immunity was responsible for the death of LECs. It was found that anti-P crystallin antibodies (Abs) killed LECs and that damage was age-dependent (Singh et al., *J. Immunol.* 155:993–999, 1995). In human serum, anti-lens Abs were more prevalent in patients with age-related cataracts (98%) than in subjects with clear lenses (40%) (Singh et al., *Exp. Eye Res.* Submitted, 1997). It was also shown that more than 96% of the sera from patients with ARC, but fewer than 30% with clear lenses, were cytotoxic. Mixing cytotoxic anti-lens Abs with whole lens antigens (Ags) decreased or eliminated the cytotoxic effects. These findings raise the possibility that human ARCs are caused by an autoimmune insult to the LECs.

There exists a need to influence favorably the physical properties of the crystalline lens.

There also exists a need to identify the gene(s) responsible for cataract and age-related cataract in particular, and to provide therapy for preventing and treating cataracts.

An object of the invention is to provide compounds that desirably influence the physical properties of the crystalline lens.

Another object of the invention is to provide therapeutics for treating diseases or conditions involving LEDGF expression.

Still another object of the invention is to provide diagnostics and research tools relating to LEDGF. These and other objects will be described in greater detail below.

SUMMARY OF THE INVENTION

We describe herein the molecular cloning and characterization of LEDGF, a novel polypeptide that stimulates protein synthesis. This increase in protein synthesis leads to the enhanced growth of a variety of cell types such as those of epithelial, epidermal or kidney origin, including lens epithelial cells. Anti-LEDGF Abs blocked the stimulatory effects of this protein, resulting in the death of LECs and other types of cells, including neuronal, fibroblasts, etc. Increased levels of anti-LEDGF Abs were found in patients with ARCs, suggesting that neutralization of LEDGF by auto-Abs is responsible for the development of cataracts and ARCs in particular.

The invention provides isolated nucleic acid molecules, unique fragments of those molecules, expression vectors containing the foregoing, and host cells transfected with those molecules. The invention also provides isolated polypeptides and agents which bind such polypeptides, including antibodies. The foregoing can be used, inter alia, in the diagnosis or treatment of conditions characterized by the aberrant expression of a LEDGF nucleic acid or polypeptide. The invention also provides methods for identifying pharmacological agents useful in the diagnosis or treatment of such conditions. Here, we present the cDNA cloning of a 61 kDa protein, LEDGF, which stimulates proliferation of a number of different cell types, particularly those of epithelial character, and include lens epithelial cells.

According to one aspect of the invention, isolated nucleic acid molecules that code for a lens epithelial cell derived growth factor polypeptide are provided and include: (a) nucleic acid molecules which hybridize under stringent conditions to a molecule consisting of a nucleic acid of SEQ ID NO:1 and which code for a lens epithelial cell derived growth factor polypeptide, (b) deletions, additions and substitutions of (a) which code for a respective lens epithelial cell derived growth factor polypeptide, (c) nucleic acid molecules that differ from the nucleic acid molecules of (a) or (b) in codon sequence due to the degeneracy of the genetic code, and (d) complements of (a), (b) or (c). In certain embodiments, the isolated nucleic acid molecule comprises nucleotides 1–3360 of SEQ ID NO:1. In some embodiments the isolated nucleic acid molecules are those comprising the human cDNA or gene corresponding to SEQ ID NO:13. The isolated nucleic acid molecule also can comprise a molecule which encodes the polypeptide of SEQ ID NO:2.

The invention in another aspect is an isolated nucleic acid molecule selected from the group consisting of (a) a fragment of a nucleic acid molecule of SEQ ID NO:1, of sufficient length to represent a sequence unique within the human genome, and identifying a nucleic acid encoding a Lens Epithelial Cell Derived Growth Factor polypeptide, (b) complements of (a), provided that the fragment includes a sequence of contiguous nucleotides which is not identical to any sequence selected from the sequence group consisting of (1) sequences having the GenBank accession numbers of Table III, (2) complements of (1), and (3) fragments of (1) and (2).

In one embodiment the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In another embodiment the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

In yet another embodiment the molecule encodes a polypeptide which, or a fragment of which, binds a human antibody.

According to another aspect, the invention involves expression vectors, and host cells transformed or transfected with such expression vectors, comprising the nucleic acid molecules described above.

According to another aspect of the invention, an isolated polypeptide is provided. The isolated polypeptide is encoded by the isolated nucleic acid molecule of claim 1, 2, or 3. In some embodiments, the isolated polypeptide is a secreted protein encoded by the nucleic acid of claim 2, comprising a polypeptide having the sequence of SEQ ID NO:2. In other embodiments, the isolated polypeptide comprises a fragment or variant of the foregoing of sufficient length to represent a sequence unique within the human genome and identifying a polypeptide that has protein synthesis induction activity, provided that the fragment includes a sequence of contiguous amino acids which is not identical to any sequence selected from the sequence group consisting of SEQ ID NO:9, SEQ ID NO:10, SEQ ID NO:11, SEQ ID NO:12, and SEQ ID NO:22. In another embodiment, immunogenic fragments of the polypeptide molecules described above are provided.

According to another aspect of the invention, isolated polypeptides are provided which selectively bind a polypeptide encoded by the nucleic acid of claim 1, 2, or 3. Preferably the isolated polypeptides selectively bind a polypeptide which comprises the sequence of SEQ ID NO:2, or fragments thereof (e.g. SEQ ID NO:4, SEQ ID NO:6 and SEQ ID NO:8). In preferred embodiments, the isolated binding polypeptides include antibodies and fragments of antibodies (e.g., Fab, F(ab)$_2$, Fd and antibody fragments which include a CDR3 region which binds selectively to the LEDGF polypeptide). In certain embodiments the antibodies are human.

According to another aspect of the invention, a method is provided for determining an individual's susceptibility to developing cataracts. A test sample containing antibodies of the individual is obtained. Anti-LEDGF antibody levels are measured in the test sample and compared to a control. The individual's risk profile of developing a cataract is characterized based upon the level of the anti-LEDGF antibody in comparison to the control. The control may be a predetermined value such as serum titer of anti-LEDGF antibodies of $OD_{492} \geq 200$. In a preferred embodiment the test sample is blood, although the test sample can also be tissue such as epidermis and buccal scrapings.

The invention also contemplates kits comprising a package including assays for anti-LEDGF antibodies, LEDGF epitopes, LEDGF nucleic acids, and instructions, and optionally related materials such as controls, for example, a number, color chart, or an epitope of the expression product of the nucleic acid of claim 1 for comparing the level of anti-LEDGF antibodies in the test sample as determined by the assay with a control value or control assay results to determine a risk of developing a cataract. The kits may also include an assay for anti-β-crystallin antibodies.

According to another aspect of the invention, a method is provided for treating subjects with an abnormally elevated level of anti-LEDGF antibodies to inhibit the development of cataracts. The method involves administering to an individual in need of such treatment a polypeptide encoded by the isolated nucleic acid molecule of claim 1, 2 or 3 having protein synthesis induction activity in an amount effective to inhibit the formation of opacities in the crystalline lens. In preferred embodiments of the invention, LEDGF polypeptides are administered orally or conjugated to antibodies and administered intra venously in an amount effective to tolerize the subject to LEDGF and to lower the risk of the subject developing a cataract. Nasal administration is also particularly contemplated.

Another aspect of the invention is a method for determining the level of LEDGF expression in a subject. Expression is defined either as LEDGF mRNA expression or LEDGF polypeptide expression. Preferred embodiments of the invention include PCR and Northern blotting for measuring mRNA expression, and monoclonal or polyclonal LEDGF antisera as part of the reagents to measure LEDGF polypeptide expression. Also in certain embodiments, tissue samples such as biopsy samples, and biological fluids such as blood, are used as the source of test samples. LEDGF expression is compared to a measured control.

The invention in a further aspect involves a method for decreasing LEDGF mediated activity in a subject. An agent that selectively binds to an isolated nucleic acid molecule of the invention or an expression product thereof is administered to a subject in need of such treatment, in an amount effective to decrease LEDGF mediated activity in the subject. Preferred agents are antisense nucleic acids, including modified nucleic acids, and polypeptides such as antibodies against LEDGF.

The invention in another aspect involves a method for decreasing LEDGF mediated activity in a subject with a cancer that expresses LEDGF. An agent that selectively binds to an isolated nucleic acid molecule of the invention or an expression product thereof is administered to a subject in need of such treatment, in an amount effective to decrease LEDGF mediated activity in the subject in order to inhibit or slow down the proliferation of cancer. Preferred agents are antisense nucleic acids, including modified nucleic acids, and polypeptides such as antibodies against LEDGF.

According to another aspect of the invention, methods for inducing cell-death are also provided. The methods involve contacting a cell with an amount of an inhibitor of LEDGF effective to inhibit LEDGF mediated activity in the cell, and induce cell-death. In certain embodiments, the inhibitor is an antisense nucleic acid which inhibits the expression of LEDGF, or a polypeptide that binds to LEDGF and blocks its activity.

According to still another aspect of the invention, methods for inhibiting a cell's differentiation both in vivo and in vitro are also provided. The methods involve contacting a mammalian cell with an amount of a LEDGF inhibitor effective to decrease LEDGF mediated activity in the mammalian cell and prevent it from differentiating. In certain embodiments, the inhibitor is an antisense nucleic acid which inhibits the expression of LEDGF, or a polypeptide that binds to LEDGF and blocks its activity.

Another aspect of the invention is a method for increasing cell proliferation. A cell expressing a LEDGF receptor is contacted with an agent that increases LEDGF stimulated cell proliferation in an amount effective to stimulate such proliferation. The agent can be a polypeptide encoded by the nucleic acid of SEQ ID NO:1. The agent can also be a polypeptide having the amino acid sequence of SEQ ID NO:2, or an LEDGF receptor stimulatory fragment thereof.

Another aspect of the invention involves a method for inducing wound healing in a subject. An agent as described in the immediately preceding paragraph is administered to a subject in need of such treatment, in an amount effective to increase LEDGF mediated activity in the subject in order to promote the proliferation of cells such as epidermal cells and accelerate wound healing.

According to still another aspect of the invention, methods for inhibiting w environmental stress-induced cell-death both in vivo and in vitro are also provided. The methods involve contacting a mammalian cell expressing a LEDGF receptor, and under environmental stress otherwise sufficient to induce cell-death, with an agent that increases LEDGF mediated activity in an amount effective to inhibit death of the mammalian cell which otherwise would result from such environmental stress. The agent can be a polypeptide encoded by the nucleic acid of SEQ ID NO:1. The agent can also be a polypeptide having the amino acid sequence of SEQ ID NO:2, or an LEDGF receptor stimulatory fragment thereof.

The methods of the invention are preferably used when increased temperatures, physical trauma, oxidative, osmotic or chemical stress, and UV irradiation form part of the environmental stress.

According to still another aspect of the invention, methods for increasing heat-shock protein activity in a cell, both in vivo and in vitro are provided. The methods involve contacting the cell with an isolated nucleic acid molecule of claim 1 or an expression product thereof, in an amount effective to increase LEDGF mediated activity in the cell and to increase heat-shock protein activity in the cell. The agent can be a polypeptide encoded by the nucleic acid of SEQ ID NO:1. The agent can also be a polypeptide having the amino acid sequence of SEQ ID NO:2, or an LEDGF receptor stimulatory fragment thereof.

The invention in another aspect provides compositions comprising an antisense nucleic acid which selectively binds to the nucleic acid of claim 1 and which reduces the expression of LEDGF, and a pharmaceutically acceptable carrier.

The present invention thus involves, in several aspects, LEDGF polypeptides, genes encoding those polypeptides, functional modifications and variants of the foregoing, useful fragments of the foregoing, as well as therapeutics and diagnostics relating thereto.

These and other objects of the invention will be described in further detail in connection with the detailed description of the invention.

BRIEF DESCRIPTION OF THE DRAWINGS

FIG. 1A shows the over-expression of LEDGF in LECs as compared to a negative control (vector alone). FIG. 1B shows that LEDGF is present (secreted) in the culture medium.

FIG. 3A shows the inhibition of $^3$H-thymidine uptake in mouse LECs by adding anti-LEDGF Abs to the medium. FIG. 3B shows the effect of anti-LEDGF Abs on the survival of human LECs.

BRIEF DESCRIPTION OF THE SEQUENCES

Figure 1:
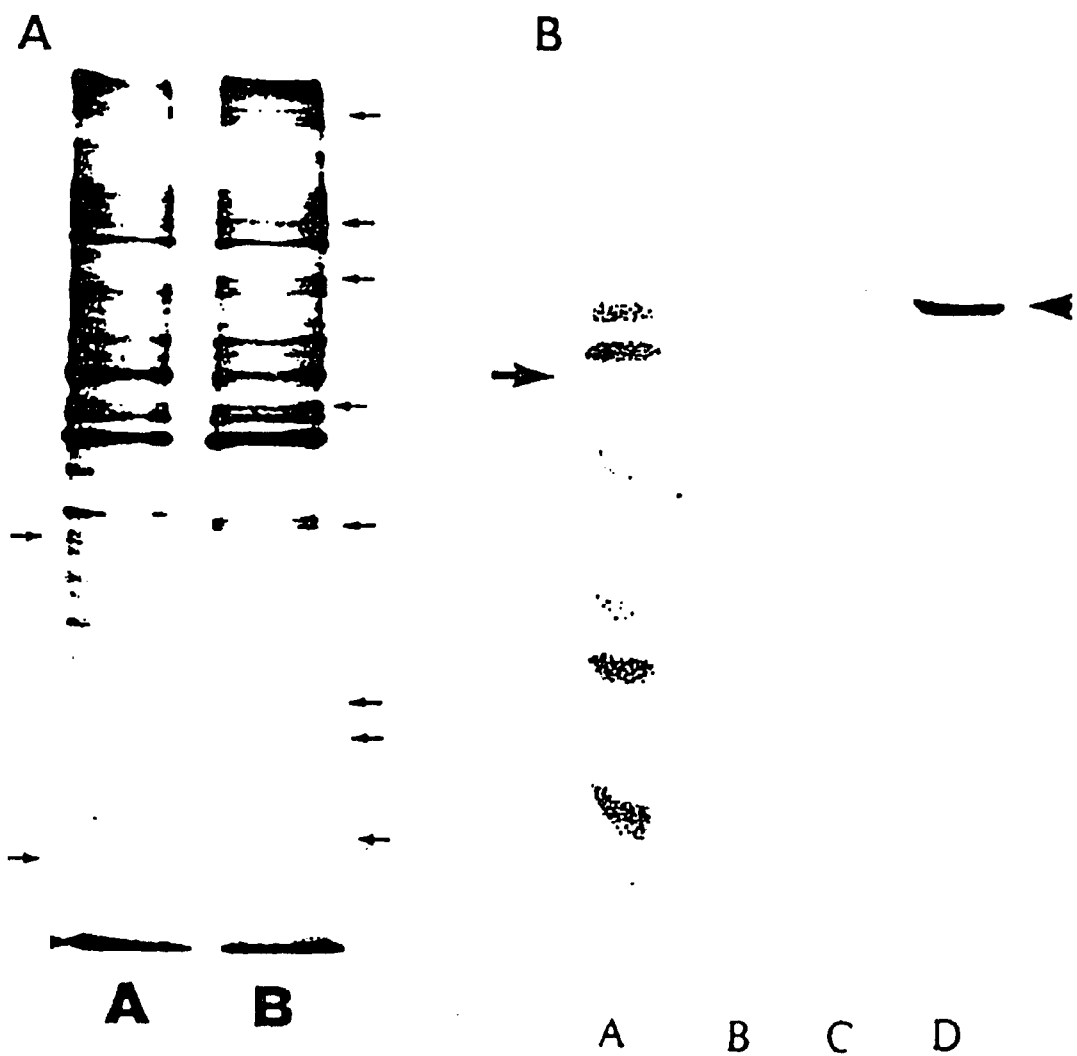
FIG. 1 shows the in vitro effects of over-expressing LEDGF in LECs.

SEQ ID NO:1 is the nucleotide sequence of the human LEDGF cDNA.

SEQ ID NO:2 is the, predicted amino acid sequence of the translation product of human LEDGF cDNA.

SEQ ID NO:3 is a unique nucleotide sequence of the 5'-end of the human LEDGF cDNA.

SEQ ID NO:4 is the predicted amino acid sequence encoded by SEQ ID NO:3.

SEQ ID NO:5 is a unique nucleotide sequence of the 3'-end of the human LEDGF cDNA.

SEQ ID NO:6 is the predicted amino acid sequence encoded by SEQ ID NO:5.

SEQ ID NO:7 is the nucleotide sequence of the human LEDGF cDNA that excludes a large portion of the 5'-end of the human LEDGF cDNA.

SEQ ID NO:8 is the predicted amino acid sequence encoded by SEQ ID NO:7 that maintains native LEDGF stimulating activity.

SEQ ID NO:9 is a contiguous sequence of 13 amino acids common to both LEDGF and HDGF.

SEQ ID NO:10 is a contiguous sequence of 15 amino acids common to both LEDGF and HDGF.

SEQ ID NO:11 is a contiguous sequence of 9 amino acids common to both LEDGF and HDGF.

SEQ ID NO:12 is a contiguous sequence of 6 amino acids common to both LEDGF and HDGF.

SEQ ID NO:13 is the nucleotide sequence of the largest open reading frame of the human LEDGF cDNA of SEQ ID NO:1 encoding for the polypeptide of SEQ ID NO:2.

SEQ ID NO:14 is the amino acid sequence of the human HDGF.

SEQ ID NO:15 is the amino acid sequence of the mouse HDGF.

SEQ ID NO:16 is the amino acid sequence of the transcription factor LFB1/HNF1.

SEQ ID NO:17 is the nucleotide sequence of the 5' noncoding-end of SEQ ID NO:1.

SEQ ID NO:18 is the nucleotide sequence of the 3' noncoding-end of SEQ ID NO:1.

SEQ ID NO:19 is a primer spanning the 5' noncoding-coding region of SEQ ID NO:1.

SEQ ID NO:20 is a primer from the 3' noncoding region of SEQ ID) NO:1.

SEQ ID NO:21 is the partial nucleotide sequence of human autoantigen DFS70, GenBank Acc. No. U94319.

SEQ ID NO:22 is the predicted amino acid sequence encoded by the nucleotide sequence of SEQ ID NO:21.

DETAILED DESCRIPTION OF THE INVENTION

One aspect of the invention involves the cloning of a cDNA encoding a Lens Epithelial Cell Derived Growth Factor (LEDGF). A lens epithelial cell derived growth factor according to the invention is an isolated nucleic acid molecule that comprises a nucleic acid molecule of SEQ ID NO:1, and codes for a protein that induces protein synthesis in an epithelial cell. A preferred factor of the invention includes additional features. For example, it induces growth of epithelial cells, and most preferably kidney, epidermal, retinal and neuronal cells too. It is a secreted protein with a molecular mass of 61 kDa, and it is necessary for survival of epithelial cells expressing it. By necessary for survival it is meant that interfering with the activity of the factor in a cell expressing the factor, such as a lens epithelial cell, results in cell-death. The sequence of the human gene is presented as SEQ ID NO:1, and the predicted amino acid sequence of this gene's protein product is presented as SEQ ID NO:2.

As used herein, a subject is a human, non-human primate, cow, horse, pig, sheep, goat, dog, cat or rodent. In all embodiments human LEDGF and human subjects are preferred.

Analysis of the sequence by comparison to nucleic acid and protein databases show that LEDGF shares a limited, localized homology (35% at the nucleotide level, 20% at the amino acid level) to the hepatoma-derived growth factor (HDGF—SEQ ID NOs:14 and 15) (Nakamura et al., *J. Biol. Chem.* 269:25143–25149, 1994). Limited homology is also shared between LEDGF and the liver specific transcriptional factor LFB1/HFN1 (SEQ ID NO:16) (Bartkowski et al., *Mol. Cell. Biol.* 13: 421–431, 1993). Extended homology is shared with the nucleic acid of SEQ ID NO:21. This molecule represents the partial nucleotide sequence of human autoantigen DFS70, GenBank Acc. No. U94319. Its 5'-end, however, is missing and no known function has been assigned to this molecule.

The invention thus involves in one aspect a lens epithelial cell derived growth factor polypeptide, the gene encoding this polypeptide, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to the invention, isolated nucleic acid molecules that code for a lens epithelial cell derived growth factor polypeptide include: (a) nucleic acid molecules which hybridize under stringent conditions to a molecule consisting of a nucleic acid of SEQ ID NO:1 and which code for a lens epithelial cell derived growth factor polypeptide, (b) deletions, additions and substitutions of (a) which code for a respective lens epithelial cell derived growth factor polypeptide, (c) nucleic acid molecules that differ from the nucleic acid molecules of (a) or (b) in codon sequence due to the degeneracy of the genetic code, and (d) complements of (a), (b) or (c).

Homologs and alleles of the LEDGF nucleic acids of the invention can be identified by conventional techniques. Thus, an aspect of the invention is those nucleic acid sequences which code for LEDGF polypeptides and which hybridize to a nucleic acid molecule consisting of the coding region of SEQ ID NO:1, under stringent conditions. The term "stringent conditions" as used herein refers to parameters with which the art is familiar. Nucleic acid hybridization parameters may be found in references which compile such methods, e.g. *Molecular Cloning: A Laboratory*

*Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of LEDGF nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet. Exemplary tools include the BLAST system. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for LEDGF related genes, such as homologs and alleles of LEDGF, a Southern blot may be performed using the foregoing conditions, together with a radioactive probe. After washing the membrane to which the DNA is finally transferred, the membrane can be placed against X-ray film or a phosphoimager plate to detect the radioactive signal.

Given that the expression of the LEDGF gene is abundant in certain human tissues, and given the teachings herein of a full-length human LEDGF cDNA clone, other mammalian sequences such as the mouse cDNA clone corresponding to the human LEDGF gene can be isolated from a cDNA library prepared from one or more of the tissues in which LEDGF expression is abundant, using standard colony hybridization techniques.

The invention also includes degenerate nucleic acids which include alternative codons isolated from a cDNA library prepared from one or more of the tissues in which LEDGF expression is abundant, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating LEDGF polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or SEQ ID NO:13 or complements of thereof. A unique fragment is one that is a 'signature' for the larger nucleic acid. For example, the unique fragment is long enough to assure that its precise sequence is not found in molecules within the human genome outside of the LEDGF nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank accession numbers listed in Table III or other previously published sequences as of the filing date of the priority document for sequences listed in the priority document.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components.

Likewise, unique fragments can be employed to produce nonfused fragments of the LEDGF polypeptides, useful, for example, in the preparation of antibodies, immunoassays or therapeutic applications. Unique fragments further can be used as antisense molecules to inhibit the expression of LEDGF nucleic acids and polypeptides, particularly for therapeutic purposes as described in greater detail below.

As will be recognized by those skilled in the art, the size of the unique fragment will depend upon its conservancy in the genetic code. Thus, some regions of SEQ ID NO:1 or SEQ ID NO:13 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 3360, or SEQ ID NO:13 beginning at nucleotide 1 and ending at nucleotide 1593, or complements thereof, that is 18 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a LEDGF polypeptide, to decrease LEDGF activity. This is desirable in virtually any medical condition wherein a reduction of LEDGF activity is desirable, including certain cancers. Antisense LEDGF molecules, in this manner, can be used to slow down or arrest the proliferation of cancer cells in vivo. When using antisense preparations of the invention, slow intravenous administration is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med.* 1(11) :1116–1118, 1995). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although, SEQ ID No:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1. Similarly, antisense to allelic or homologous LEDGF cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding LEDGF polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for LEDGF proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *E. coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its, ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding LEDGF polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.PIA recombinant is disclosed by Wamier et al., in intradermal injection in mice for immunization against P1A (*Int. J. Cancer*, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, LEDGF cDNA sequence containing expression vectors, to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The invention also permits the construction of LEDGF gene "knock-outs" in cells and in animals, providing materials for studying certain aspects of LEDGF activity.

The invention also provides isolated polypeptides (including whole proteins and partial proteins), encoded by the foregoing LEDGF nucleic acids, and include the polypeptide of SEQ ID NO:2 and unique fragments thereof. Such polypeptides are useful, for example, alone or as fusion proteins to stimulate cell proliferation, to maintain cell survival, to generate antibodies, as components of an immunoassay, etc. polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of an LEDGF polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length, 530 amino acids long). Virtually any segment of SEQ ID NO:2, excluding the ones that share identity with HDGF (SEQ ID NOs:9, 10, 11 and 12) and the partial human autoantigen DFS70 (SEQ ID Nos:22), that is 9 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding to receptors, and protein synthesis stimulating activity. One important activity is the ability to act as a signature for identifying the polypeptide. Another is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the LEDGF polypeptides described above. As used herein, a "variant" of a LEDGF polypeptide is a polypeptide which contains one or more modification to the primary amino acid sequence of a LEDGF polypeptide. Modifications which create a LEDGF polypeptide variant are typically made to the nucleic acid which encodes the LEDGF polypeptide, and can include deletions, point mutations, truncations, amino acid substitutions and addition of amino acids or non-amino acid moieties to: 1) reduce or eliminate an activity of a LEDGF polypeptide; 2) enhance a property of a LEDGF polypeptide, such as protein stability in an expression system or the stability of protein-protein binding; 3) provide a novel activity or property to a LEDGF polypeptide, such as addition of an antigenic epitope or addition of a detectable moiety; or 4) to provide equivalent or better binding to a LEDGF polypeptide receptor or other molecule (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the LEDGF amino acid sequence. One of skill in the art will be familiar with methods for predicting the effect on protein conformation of a change in protein sequence, and can thus "design" a variant LEDGF polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

Variants can include LEDGF polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a LEDGF polypeptide by eliminating proteolysis by proteases in an expression system (e.g., dibasic amino acid residues in yeast expression systems in which KEX2 protease activity is present).

Mutations of a nucleic acid which encodes a LEDGF polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant LEDGF polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a LEDGF gene or cDNA clone to enhance expression of the polypeptide.

The skilled artisan will realize that conservative amino acid substitutions may be made in LEDGF polypeptides to provide functionally equivalent variants of the foregoing polypeptides, i.e., the variants retain the functional capabilities of the LEDGF polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the LEDGF polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of LEDGF polypeptides, i.e., variants of LEDGF polypeptides which retain the function of the natural LEDGF polypeptides, are contemplated by the invention. Conservative amino-acid substitutions in the amino acid sequence of LEDGF polypeptides to produce functionally equivalent variants of LEDGF polypeptides typically are made by alteration of a nucleic acid encoding LEDGF polypeptides (SEQ ID NOs: 1, 13). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a LEDGF polypeptide. The activity of functionally equivalent fragments of LEDGF polypeptides can be tested by cloning the gene encoding the altered LEDGF polypeptide into a bacterial or mammalian expression vector, introducing the vector into an appropriate host cell, expressing the altered LEDGF polypeptide, and testing for a functional capability of the LEDGF polypeptides as disclosed herein.

The invention as described herein has a number of uses, some of which are described elsewhere herein. First, the invention permits isolation of LEDGF polypeptides. A variety of methodologies well-known to the skilled practitioner can be utilized to obtain isolated LEDGF molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of LEDGF mRNA in cell-free extracts such as the reticulocyte lysate system also may be used to produce LEDGF polypeptides. Those skilled in the art also can readily follow known methods for isolating LEDGF polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from LEDGF polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of cancer associated antigens, especially those which are similar to known proteins which have known activities, one of ordinary skill in the art can modify the sequence of the cancer associated antigens by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The isolation of the LEDGF cDNA also makes it possible for the artisan to diagnose a disorder characterized by an aberrant expression of LEDGF. These methods involve determining expression of the LEDGF gene, and/or LEDGF polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted LEDGF protein.

The invention also embraces isolated peptide binding agents which, for example, can be antibodies or fragments of antibodies having the ability to selectively bind to LEDGF polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to LEDGF polypeptides, and complexes of both LEDGF polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the LEDGF polypeptide or a complex of LEDGF and a binding partner. This process can be repeated through several cycles of reselection of phage that bind to the LEDGF polypeptide or complex. Repeated rounds lead to enrichment of phage bearing particular sequences. DNA sequence analysis can be conducted to identify the sequences of the expressed polypeptides. The minimal linear portion of the sequence that binds to the LEDGF polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the LEDGF polypeptides. Thus, the LEDGF polypeptides of the invention, or a fragment thereof, or complexes of LEDGF and a binding partner can be used to screen peptide libraries, including phage display libraries, to identify and select peptide binding partners of the LEDGF polypeptides of the invention. Such molecules can be used, as described, for screening assays, for purification protocols, for interfering directly with the functioning of LEDGF and for other purposes that will be apparent to those of ordinary skill in the art.

A LEDGF polypeptide, or a fragment thereof, also can be used to isolate their native binding partners. Isolation of binding partners may be performed according to well-known methods. For example, isolated LEDGF polypeptides can be attached to a substrate, and then a solution suspected of containing an LEDGF binding partner may be applied to the substrate. If the binding partner for LEDGF polypeptides is present in the solution, then it will bind to the substrate-bound LEDGF polypeptide. The binding partner then may be isolated. Other proteins which are binding partners for LEDGF, may be isolated by similar methods without undue experimentation.

The invention also embraces determining an individual's susceptibility to developing cataracts. In determining an individual's susceptibility to developing cataracts, the level of anti-LEDGF antibodies in the individual is obtained. The level of the anti-LEDGF antibodies for the individual can be obtained by numerous art recognized methods. Typically, the anti-LEDGF antibody level is determined by immunoassays, such as enzyme-linked immunoassays, or other conventional techniques. The invention enables such techniques through isolation of LEDGF and epitopes thereof. The presence and level of anti-LEDGF antibodies can be determined as a measure of binding to isolated LEDGF or epitopes thereof. These techniques are performed on test samples obtained from the individual's bodily fluids, such as blood, lymph, saliva, urine and the like, tissues, or cultures from tissue biopsies. The preferred body fluid is blood and the preferred tissue is skin or buccal scraping.

The invention also involves comparing the anti-LEDGF antibody level for the individual with a control. The control can be of any art recognized type, such as reagents to be tested side by side with the test fluid or a predetermined value such as a color or a number.

The predetermined value can be a single cut-off value, such as the median or mean anti-LEDGF antibody level for a control population. The control population preferably includes only individuals of a similar age group as the individual tested (e.g. within 5–10 years). The predetermined value can also be a range, for example, where the population used to obtain the anti-LEDGF antibody level to be used as the control, is divided equally (or unequally) into groups, such as a low-risk group and a high-risk group, or into quadrants, the lowest quadrant being individuals with the lowest risk and the highest quadrant being individuals with the highest risk. Thus, the predetermined value can depend upon the particular population selected. For example, an apparently healthy population (no detectable disease and no prior history of cataracts) can have a different 'normal' range of anti-LEDGF antibody levels than will a population the members of which have had a prior cataract disorder. Accordingly, the predetermined values selected may take into account the category in which an individual falls. Appropriate ranges and categories can be selected with no more than routine experimentation by those of ordinary skill in the art.

For anti-LEDGF antibody levels, one important cut-off for a population of apparently healthy individuals is $OD_{492}<200$. In characterizing risk, individuals with anti-LEDGF antibody levels equal to or higher than the foregoing mentioned cut-off value are more susceptible to developing a cataract than individuals with anti-LEDGF antibody levels below this value.

Figure 5:
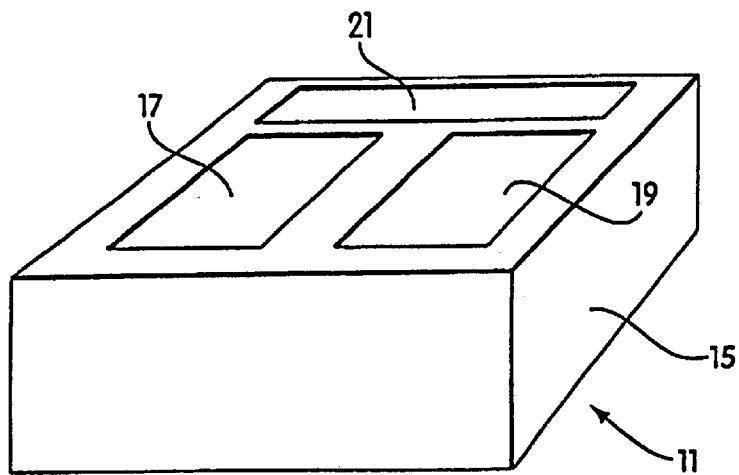
FIG. 5 depicts a kit (11) comprising packaging (15), an agent of the invention (17) (e.g., anti-LEDGF Abs, LEDGF epitopes, etc.), a control agent (19), and instructions (21) for utilizing such agents in diagnostic or therapeutic applications.

The invention also provides novel kits which could be used to measure the levels of the nucleic acids of the invention, expression products of the invention or anti-LEDGF antibodies. In the case of nucleic acid detection, pairs of primers for amplifying LEDGF nucleic acids can be included. The preferred kits would include controls such as known amounts of nucleic acid probes, LEDGF epitopes (such as LEDGF expression products) or anti-LEDGF antibodies, as well as instructions or other printed material. In certain embodiments the printed material can characterize risk of developing a cataract based upon the outcome of the assay. Additionally, anti-β-crystallin antibodies and β-crystallin epitopes can also be included for control purposes. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with LEDGF protein and a container containing labeled anti-human IgG antibodies. A well of the plate is contacted with, for example, serum, washed and then contacted with the anti-IgG antibody. The label is then detected. A kit embodying features of the present invention, generally designated by the numeral 11, is illustrated in FIG. 5. Kit 11 is comprised of the following major elements: packaging 15, an agent of the invention 17, a control agent 19 and instructions 21. Packaging 15 is a box-like structure for holding a vial (or number of vials) containing an agent of the invention 17, a vial (or number of vials) containing a control agent 19, and instructions 21. Individuals skilled in the art can readily modify packaging 15 to suit individual needs.

The invention also involves a method for treating subjects at risk of developing cataracts (i.e. with an abnormally elevated level of anti-LEDGF antibody) or subjects having had capsulotomy, to prevent the formation of future cataracts. This method involves the administration of an agent to 'tolerize' the subject against LEDGF epitopes. It has been described in the art that by administering an antigen to a mammal over an extended period of time or in certain doses and regimens, Th1-type immunoreactive responses to the antigen are suppressed leading to tolerization. A preferred agent of the invention administered is a LEDGF polypeptide encoded by the isolated nucleic acid molecules of claim 1, 2 or 3. The preferred mode of its administration is oral. Another preferred agent for the purpose of tolerization is a LEDGF polypeptide encoded by the isolated nucleic acid molecules of claim 1, 2 or 3 conjugated to an antibody. The preferred mode of administration for this agent is intravenously. The agents described herein are administered in effective amounts. An effective amount of the agent is that dosage sufficient to reduce a subject's immune response against LEDGF polypeptides, and thus reduce anti-LEDGF serum antibody levels in order to prevent opacity formation in the crystalline lens of the subject.

The invention also provides methods to measure the level of LEDGF expression in a subject. This can be performed by first obtaining a test sample from the subject. The test sample can be tissue or biological fluid. Tissues include lens epithelium, kidney and skin, and biological fluids include blood, aqueous humor and tears. Both invasive and non-invasive techniques can be used to obtain such samples and are well documented in the art. At the molecular level both PCR and Northern blotting can be used to determine the level of LEDGF mRNA using products of this invention described earlier, and protocols well known in the art that are found in references which compile such methods. At the protein level, LEDGF expression can be determined using either polyclonal or monoclonal anti-LEDGF sera in combination with standard immunological assays. The preferred methods will compare the measured level of LEDGF expression of the test sample to a control. A control can include a known amount of a nucleic acid probe, a LEDGF epitope (such as a LEDGF expression product), or a similar test sample of a subject with a control or 'normal' level of LEDGF expression.

The invention also embraces a method for treating subjects with cancers expressing LEDGF. It involves first determining whether the cancer expresses LEDGF. If it does, then an effective amount of an agent which interferes with LEDGF mediated activity can be administered to the subject in order to slow down, or inhibit, the proliferation of the cancer cells expressing LEDGF. Such agents include antisense oligonucleotides (e.g. to the nucleic acid of SEQ ID NO:1) or a polypeptide that binds to LEDGF (such as an anti-LEDGF antibody). The mode of administration and dosage of the agent will vary with the particular stage of the condition being treated, the age and physical condition of the subject being treated, the duration of the treatment, the nature of the concurrent therapy (if any), the specific route of administration, and the like factors within the knowledge and expertise of the health practitioner. In preferred embodiments of the invention cancers expressing LEDGF include: biliary tract cancer, brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In other embodiments cancers expressing LEDGF are cancers aberrantly expressing LEDGF. Aberrant expression is overexpression of LEDGF.

In certain embodiments the agent can be administered, as mentioned earlier, in combination with other anti-cancer agents such as: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin;

Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safmgol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The invention also contemplates methods for decreasing LEDGF activity in a subject. Such subjects may have abnormally high LEDGF levels, for example, such subjects may have conditions characterized by unwanted proliferation of cells, and in tissues and cells not usually expressing LEDGF at all or typically at lower levels (e.g. cancer cells). In other embodiments, LEDGF activity is decreased in order to slow down or inhibit such unwanted proliferation (e.g. in disorders such as restenosis and psoriasis). Decrease in LEDGF activity in the subject can be accomplished by the administration of an agent that interferes with LEDGF mediated activity. Such agents bind to the nucleic acid of SEQ ID NO:1 or expression products thereof, in amounts effective to slow down or inhibit the proliferation of cells expressing LEDGF. A preferred agent is an antisense oligonucleotide or a polypeptide that binds to LEDGF (such as an anti-LEDGF antibody). As in the method for treating cancers expressing LEDGF, the mode of administration and dosage of the agent will vary with the particular stage of the condition being treated, the age and physical condition of the subject being treated, the duration of the treatment, the nature of the concurrent therapy (if any), the specific route of administration, and the like factors within the knowledge and expertise of the health practitioner.

The invention also contemplates methods for preventing the differentiation of cells in vitro. Cells in vitro are contacted with an agent that selectively binds to the products of this invention, such as the isolated nucleic acid of claim 1, 2 or 3, or its expression products thereof, in an amount effective to decrease LEDGF mediated activity in the cell and inhibit its differentiation. The agent can be an antisense oligonucleotide or a polypeptide (anti-LEDGF antibody), as described earlier. Such methods can be very useful in preventing the differentiation of a number of mammalian cell types in vitro, for example, mouse embryonic stem cells used in "knock-out" experiments, hemopoietic stem cells, etc.

By using the methodology as described in the preceding paragraphs, but with increased effective amounts of the agent, the invention also provides for a method to induce cell-death both in vivo and in vitro. In this instance, the agents that interfere with LEDGF mediated activity are administered in amounts effective to induce cell-death of cells expressing LEDGF.

For in vivo treatments localized administration is called for in this embodiment.

The invention also embraces methods for increasing cell proliferation by contacting a cell expressing a LEDGF receptor with the isolated nucleic acid of claim 1, 2 or 3, or expression products thereof, in an amount effective to increase LEDGF activity in the cell and promote its proliferation. Such methods can be very useful in the expansion of mammalian cell cultures, including differentiated cells, and to promote the proliferation of cells involved in wound healing, both in vivo and in vitro. Thus, the invention also involves methods for treating a subject with a wound to induce wound healing by contacting the wound with an agent that increases LEDGF mediated activity in amounts sufficient to promote cell proliferation and wound healing. The preferred agent is LEDGF or an active fragment thereof. A cell expressing a LEDGF receptor is a cell that upon contact with LEDGF increases its protein synthesis.

The invention also provides methods for inhibiting cell-death induced by environmental stress of a cell which expresses a LEDGF receptor, by contacting it with the isolated nucleic acid of claim 1, 2 or 3, or expression products thereof, in an amount effective to increase LEDGF mediated activity in the cell and enhance its survival ability, both in vivo and in vitro. The lifespan of a cell under environmental stress is significantly shorter when compared to the lifespan of a cell under no such stress. This can be easily detected by placing a number of cells under a form of environmental stress and comparing their survival (numbers) to an identical number of cells free from any stress over a period of time. The amount of the foregoing agent(s) of the invention sufficient to inhibit cell-death, is the amount sufficient to extend the lifespan of the mammalian cell under environmental stress toward comparable lifespan lengths of cells free from any environmental stress. Such methods can be used to protect cells from environmental insults, such as increased temperatures (e.g., fever), physical trauma, oxidative, osmotic and chemical stress, and UV irradiation. In a preferred embodiment of this invention cells under environmental stress are skin fibroblasts, and topical skin applications with an agent that increases LEDGF mediated activity in amounts sufficient to promote cell survival are contemplated. In another preferred embodiment cells under environmental stress are neuronal cells. The preferred agent is LEDGF or an active fragment thereof.

The invention also provides methods for increasing heat-shock protein activity in a cell, by contacting it with the isolated nucleic acid of claim 1, 2 or 3, or expression products thereof, in an amount effective to increase LEDGF mediated activity in the cell and to increase heat-shock protein activity in the cell, both in vivo and in vitro. By "increased heat-shock protein activity" it is meant to include both increases in a heat-shock protein mRNA expression and heat-shock protein polypeptide production. In preferred embodiments $\alpha\beta$-crystallin and HSP-27 activity is increased. The preferred agent is also LEDGF or an active fragment thereof.

The pharmaceutical preparations, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a decrease in cell proliferation. In other cases, it is an increase in cell proliferation. In still other cases, it is a decrease in a subject's immune hypersensitivity to LEDGF as evidenced by a decrease in circulating anti-LEDGF antibodies.

Generally, doses of active compounds of the present invention would be from about 0.01 mg/kg per day to 1000 mg/kg per day. It is expected that doses ranging from 50–500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The LEDGF polypeptides or fragments thereof may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

LEDGF polypeptides preferably are produced recombinantly, although such polypeptides may be isolated from biological extracts. Recombinantly produced LEDGF polypeptides include chimeric proteins comprising a fusion of a LEDGF protein with another polypeptide, e.g., a polypeptide capable of providing or enhancing protein-protein binding, sequence specific nucleic acid binding (such as GAL4), enhancing stability of the LEDGF polypeptide under assay conditions, or providing a detectable moiety, such as green fluorescent protein. A polypeptide fused to a LEDGF polypeptide or fragment may also provide means of readily detecting the fusion protein, e.g., by immunological recognition or by fluorescent labeling.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

EXAMPLES

Experimental Procedures

Construction and Screening of the cDNA Library

One hundred human lens capsulotomy specimens were obtained from Dr. Joseph Horwitz, Jules Stein Eye Institute, UCLA. Total RNA extraction, mRNA purification and cDNA construction were performed according to methods well known in the art. The double stranded cDNAs were subcloned into the EcoRI and XhoI sites of the Uni-ZAP™ XR vector of the ZAP-cDNA Synthesis Kit (Stratagene, La Jolla, Calif.) as described in the manual of the manufacturer. The library titre was $4 \times 10^6$ plaque forming units per 1 mg of cDNA. The background of this library was less then 2%. The library was screened with Ab probes in human sera (1:200 dilution) from cataract patients. The second Ab used was goat anti-human IgG labeled with horseradish peroxidase (1:5,000 dilution; Kirkegaard & Perry Laboratories, Inc.,) and color-developed with 0.01% hydrogen peroxidase and 0.05% 3,3-diamino-benzidine-tetrahydrochloride (DAB; Sigma Chemical Co., St Louis, Mo.) as recommended by the manufacturer (Kirkegaard & Perry Laboratories, Inc.). Positive phagemid bluescript SK(−) clones were identified and cDNAs were purified as described in the manual of the kit manufacturer (ExAssist/Solar System; Stratagene, La Jolla, Calif.).

DNA and Protein Sequence Determination

DNA sequence was determined in the Brigham and Women's Hospital Automated Sequencing and Genotyping Facility. Molecular biological techniques such as restriction enzyme treatment, subcloning, DNA extraction, bacterial culture and purification of DNA fragments were performed according to methods well known in the art and as described in references which compile such methods. Computer analyses of protein and DNA sequences was done using the GCG "Idea" program (Kaneshisa, National Cancer Institute, Frederick, Md., 1986). Restriction endonucleases, expression vectors, and modifying enzymes were purchased from commercial sources (Gibco-BRL). Sequencing vectors for DNA were purchased from Stratagene (La Jolla, Calif.). Oligonucleotide probes were purchased from Lofstrand Labs Limited (Gaithersburg, Md.).

Northern Blot Analysis

Poly(A)-RNA for northern blot analysis was isolated from mouse cultured lens epithelial cell and from various mouse organs (liver, spleen, thymus, lymphocytes, heart, kidney, lung, brain, and muscles). Approximately 5 $\mu$g of each poly(A)RNA was applied to a well of 1% agarose-formaldehyde gel electrophoresis. The resulting RNAs were blotted to a nitrocellulose membrane (Optitran™; Schleicher & Schuell, Keene, N.H.). The RNA on the membrane was hybridized at 42° C. in 50% formamide with $^{32}$P-labeled HLC10 cDNA probe. Duplicate lanes of RNA, run in parallel, were hybridized with $^{32}$P-labeled β-actin cDNA probe.

Cell Culture

Mouse LECs were grown in a six well-plate ($5 \times 10^6$ cells/well) in DMEM containing 10% FCS. For studies of protein synthesis, we used [$^{35}$S]-methionine (New England Nuclear—NEN, Boston, Mass.) incorporation. Medium was aspirated from the wells and washed twice by gently swirling with methionine/cysteine-free DMEM-medium. Cells were starved for 30 minutes at 37° C. to deplete intracellular pools of methionine. Then $^{35}$S-methionine (150 µCi/ml;) was added in the medium and incubated for 12 hr.

Cells were trypsinized (0.25% trypsin and 1 mM EDTA-Na in PBS) for 5–10 minutes at room temperature and separated from the bottom of flask. After washing with PBS, the cells were cultured in Dulbecco's Modified Eagle Medium (DMEM) (Gibco-BRL) supplemented with heat-inactivated fetal calf serum (FCS) (10% for mouse LECs and 20% for human LECs), 1 mM L-glutamine, 25 mM HEPES, 100 unit/ml penicillin, 100 µg/ml streptomycin (Cat. No. 1196S-050; Gibco-BRL) at 37° C. in a 5% $CO_2$ atmosphere. The medium was replaced every third day (Ibaraki, I., et al., *Exp. Eye Res.*, 1997, 64:229–238; Reddy et al., *Exp. Eye Res.*, 1988, 47:465–78).

Expression of LEDGF in a Prokarvotic Vector and its Purification

The plasmid of identified full length cDNA clone (HLC 10) was digested with restriction enzymes BamHI and EcoRI (Gibco-BRL), and the fragment was ligated into the BamIi and EcoRI sites of a pGEX-2T vector (Pharmacia Biotech, Piscataway, N.J.). The construct was transfected in *E. coli* (BL21). The transformed *E. coli* was cultured in 500 ml of LB-ampicillin medium and incubated at 35° C. with shaking until optical density of *E. coli* reached to 0.5 $OD_{490}$. Then, isopropyl b-D-thiogalactoside (IPTG) (Pharmacia Biotech, Piscataway, N.J.) was added at final concentration 100 µM and further incubated 5–6 hr. Bacteria were centrifuged at 6,000 rpm for 20 min at 4° C. Pellet was suspended in 25 ml of the lysis buffer (50 mM Tris-HCL, pH8.0; 200 mM NaCl, 1.5 mM EDTA, and 1 mM PMSF) followed by addition of lysozyme (1 mg/ml) and incubated on ice for 15 min. Then, Triton X-100 (Sigma Chemicals) was added at the final concentration of 1% and mixed gently for 30 min to aid the solubilization of fusion protein. The lysate was sonicated with short bursts. The sonicate was centrifuged at 12,000 rpm for 10 min at 4° C. Supernatant was treated with 10 mM $MgSO_4$ and 2 mM ATP at 37° C. for 10 min to disrupt the association of the 70 kDa protein to glutathione Sephrose 4B (Pharmacia Biotech) during affinity chromatography. To purify the fusion protein, the supernatant was incubated over night with 2 ml of the 50% slurry of Glutathione Sepharose 4B at 4° C. Suspension was centrifuge at 500 g for 5 minutes. Pellet was washed 4 times in lysis buffer and the fusion protein was eluted with Glutathione elution buffer. The identity of the eluted protein was confirmed by SDS-PAGE and immunobloting using GST Ab (Pharmacia Biotech). Protein was dialyzed against 2,000 volumes of PBS at 4° C. Protein concentration was determined using the Bradford method (Bradford, *Anal. Biochem.*, 1976, 72:248–254). Expression in the above vector produced a relatively low level of LEDGF. To remove the 5'-noncoding region (310 bps), we prepared a construct as follows. First we created a BamHI site just before the initiation site ATG (311 nucleotide of SEQ ID NO:1) at the 5'-noncoding region (Primer: 5'-cccc ggatccatgactcgcgatttcaaacct-3': SEQ ID NO:19), and an EcoRI site (Primer: 5'-tcttgaattcgtagctgcaggtcgtcctct-3': SEQ ID NO:20) at the 3'-end. This fragment, 576 bp long, was ligated into the pGEX2T vector (Pharmacia Biotech) between the BamHI and EcoRI sites. This recombinant plasmid was amplified and the expression of LEDGF assayed by SDS-PAGE and immunobloting using GST Ab. To achieve full length LEDGF, we generated another construct where the original LEDGF cDNA was cut with EcoRI and XhoI (Gibco-BRL) and the resulting fragment of 2,153 bp was ligated into the EcoRI site of the previous construct. This construct did not contain the 5'-noncoding region, but it had an entire coding sequence. The construct was transfected into *E. coli* (BL21), and LEDGF expression was analyzed with anti-LEDGF Abs (C- and N-terminal) as well as with GST Ab (Pharmacia Biotech). The expressed protein constituted more than 10% of the total bacterial protein. The LEDGF was purified directly from the bacterial lysate using the affinity matrix Glutathione Sepharose® 4B (Pharmacia Biotech). GST-LEDGF was reduced with glutathione for the elution of the fusion protein from the affinity matrix. The eluted fusion protein, under mild and non-denaturing conditions, was cleaved with thrombin protease. The glutathione was removed by passage through the affinity matrix Glutathione Sepharose® 4B. The detailed protocol is described in the manual provided by the supplier (Pharmacia Biotech).

Cell Transformation Using Mammalian Expression Vectors

A fragment of LEDGF cDNA clone spanning the entire coding-sequence was subcloned into a pcDNA3 mammalian expression vector (Invitrogen, Carlsbad, Calif.), at the EcoRI site. This expression vector had a CMV (human cytomegalovirus) promoter which drove the expression of the inserted gene. Also it had a neomycin-selectable marker, expressed by the SV40 promoter, and used for the selection of stable transformed cell lines in the presence of G418 (geneticin, Sigma Chemical Co., St Louis, Mo.). LECs and COS7 cells were plated at a density of $5 \times 10^5$ cells per 60 mm dish. On the next day, media were replaced with 6 ml of fresh DMEM with 10% FCS. After a 4 hr incubation, these cells were transfected using the calcium phosphate method as suggested. The transfected cells were further incubated in presence of geneticin at 500 µg/ml for up to 30 days. Cells transfected with pcDNA3 vector served as a control.

Immunization of Animals

Mice (Harlan Sprague-Dawley, Indianapolis, Ind.) were injected with 100 µg LEDGF emulsified with CFA (Gibco-BRL, Bethesda, Md.) at base of the tail. Subsequently booster injections, each at a dose of 100 µg emulsified with IFA (Gibco-BRL), were carried out biweekly. The mice were euthanized by the 5th week, and serum was obtained from blood drawn from the hearts. We also immunized 2 rabbits (Harlan Sprague-Dawley) with 5.0 mg of each synthetic peptide or fusion protein emulsified with CFA (total volume 0.2 ml), and we injected these Ags into the backs of rabbits; two booster injections of 2.0 mg Ag emulsified with IFA were given at two week intervals. The peptides were conjugated with keyhole-limpet hemocyanin using the formaldehyde method (Harlow and Lane, *Antibodies: A Laboratory manual*. Cold Spring Harbor Laboratory Press. 1988, pp. 471–511), and dialyzed over night in the PBS prior to emulsification. The rabbit serum collection was five weeks after the first injection.

Phosphorylation of LEDGF

Mouse LECs ($5 \times 10^6$ cells) were cultured in $PO_4$-free DMEM (Gibco-BRL/LTI, Rockville, Md.) supplemented with 3% dialyzed FCS and starved for 15 minutes at 37° C.

Inorganic $^{32}\beta$-orthophosphate (500 $\mu$Ci/ml; NEN) adjusted to HEPES-buffer, was added and the cells were kept in culture for another 2 hrs. Cells were precipitated by centrifugation (1,200 rpm for 10 minutes), lysed with Nonidet $\beta$-40 lysis medium (Sigma Chemical Co. St Louis, Mo.) at the end of the labeling, and prepared for immunoprecipitation. Anti-LEDGF Abs (100 ml) were added and incubated overnight at 4° C. The precipitates were washed three times with PBS, were dissolved in SDS-PAGE buffer, and applied to the SDS-PAGE (8% polyacrylamide). One gel was used for immunostaining with anti-LEDGF Ab; the other gel was used for autoradiography, after staining it with Coomassie Brilliant Blue R-250 (Schwarz/Mann Biotech. Cleveland, Ohio) and drying it.

ELISA Analysis

Antibody titration was carried out by the indirect enzyme-linked immunosorbent assay (ELISA). Ninety six-well microtiter plates (Dynatech Laboratories, Alexandria, Va.) were coated with LEDGF polypeptides (0.5 mg/100 ml in sodium carbonate buffer, pH 9.3) and left overnight at 4° C. The plates were then washed 3 times with PBS containing 0.05% Tween-20 and blocked with 5% dry milk for 2 hrs at 37° C. The plates were washed and incubated again overnight at 4° C. with test sera samples (diluted $1:10^4$–$1:10^7$ in PBS with 1% dry milk). The plates were washed, and 100 $\mu$l of peroxidase-conjugated goat anti-human IgG (Kirkegaard & Perry Laboratories, Inc., Gaithersburg, Md.) at 1:2,000 dilution in PBS with 0.05% Tween-20 and 1% dry milk, were added. The plates were incubated for 2 hrs at 37° C. The plates were then washed 3 times with PBS containing 0.05% Tween-20. Then, 100 $\mu$l of O-phenylenediamine (0.4 mg/ml in citrate phosphate buffer containing 0.015% hydrogen peroxide; Sigma Chemical Co. St Louis, Mo.), were added to each well, and the reaction was stopped by the addition of 2.5N HCl. After 15 minutes the optical density at 492 nm ($OD_{492}$) was measured using a EL308 ELISA reader (Bio-Tek Instruments, Winooski, Vt.). The titer expressed in $OD_{492}$ unit was calculated as a multiple of the dilution in the linear portion of the standard plot.

Cytotoxicity Assays

Mouse LECs cultured for 1–4 days were used to study the cytotoxic potential of the Abs by the dye exclusion test. The LECs which were attached to the MULTIWELL™ tissue culture plates (Falcon, Franklin Lake, N.J.) were incubated in DMEM containing Abs at various dilutions with or without guinea pig complement (Gibco-BRL; diluted 1/10) for 3 hrs. Two control experiments were done, one in DMEM, and the other in DMEM plus normal mouse serum at the concentration of 1/40. LECs were harvested after trypsinization and subjected to the Trypan blue dye exclusion test.

Protein Isolation

Mouse LEC proteins were fractionated as described elsewhere (Ibaraki, I., et al., *Exp. Eye Res.*, 1997, 64:229–238). Synthetic peptides or Ags were purchased from a commercial source (Bio-Synthesis, Inc., Louisville, Tex.). Purification of inmunoglobulins (IgG and IgM) was conducted as described previously (Singh et al., *J. Immunol.* 155:993–999, 1997). The eluted IgG and IgM and FCS were heat treated at 56° C. for 30 min to inactivate residual complement.

Protein Blot Analysis

Water soluble proteins were dissolved in SDS-PAGE sample buffer, separated on SDS-PAGE, and then blotted onto Immobilon™-P (Millipore Corp. Bedford, Mass.) (LeGendre, *Biotechniques*, 1990, 9:788–805). The filters were incubated overnight with Abs (dilution 1:10–1:10,000) and washed. The secondary Ab was goat anti-human, mouse or rabbit IgG labeled with horseradish peroxidase (dilution 1:5,000; Kirkegaard & Perry Laboratories, Inc., Gaithersburg, Md.), and the color was developed with 0.01% hydrogen peroxide and 0.05% 3,3-diaminobenzidine-tetra hydrochloride (DAB; Bio-Rad Lab., Hercules, Calif.). Protein size markers were purchased from Bio-Rad Laboratories.

Cell Proliferation and $^3$H-Thymidine Uptake Assays

Assays for cell growth were performed as follows: Mouse LECs were seeded at a density of $2\times10^4$ cells/well in 96 well micro plates. Cells were maintained in DMEM with 10% FCS. Human cataract sera at various concentrations were added in triplicated well. Non-cataractous sera served as controls. Plates were kept in an incubator maintained at 37° C. and 6% $CO_2$ for 12 hrs. Cells were pulsed thereafter with $^3$H-thymidine (1 $\mu$Ci/well, NEN) for 16 hrs. The radioactivity incorporated into the DNA was precipitated with 1% trichloroacetic acid (Mallinckrodt, Inc., Paris, KN), and counted in a liquid scintillation counter.

Immunohistochemistry

For immunochemistry, human or mouse LECs were cultured in DMEM as described above, dissociated with 0.05% trypsin, and then fixed with 4% paraformaldehyde in 0.01 M phosphate-buffered saline (PBS: pH 7.4) for 2 hrs. After washing three times in PBS, they were blocked with 10% goat serum in PBS for 1 hr, and incubated with rabbit anti-LEDGF Ab (1:100 dilution in PBS) for 12 hrs at 4° C. After washing three times in PBS for a total of minutes, they were treated with goat anti-rabbit IgG and HRP (1:2,000 dilution in PBS; Kirkegaard & Perry Laboratories, Inc.,) for 1 hr. They were washed three times in PBS for a total of 45 min and then incubated with DAB for 5 min.

Cataract Assessment in Patients

Type and severity of cataract were graded using the Lens Opacity Classification System (LOCS III) (Chylack et al., *Arch. Ophthalmol.*, 1993, 111, 831–836). A cataract was defined as present in our patients if the LOCS III NO score was >1.8 and/or the LOCS III C score was >0.2 in either or both eyes.

Cell Culture Under Environmental Stress Conditions

Mouse LECs were grown as described earlier. Wild type LECs and LECs transformed with the appropriate expression vector (See later description) were cultured under stress conditions as follows: 50,000 cells of each cell type were cultured (in triplicate) on 24-well culture plates in 0.5 ml of DMEM with 10% FCS at 37° C. After the attachment of cells to the bottom of the well (16 hrs), the cells were washed twice with DMEM and further cultured in 0.5 ml DMEM without serum at either 41° C. (for hyperthermic stress) or 37° C. with various concentration of $H_2O_2$ (for hyper-oxidative stress). In the hyperthermic stress experiment, the cell viability was monitored at day 0, 1, 3, and 7, after trypsinization with 0.5 ml of trypsin-EDTA and 1 ml of trypan blue staining to evaluate cell death. In the hyper-oxidative stress experiment, the cells were monitored at 0, 2, 6, and 24 hrs after addition of $H_2O_2$. We calculated the percent of living cells from the ratio of the trypan blue unstained cell number to the total cell number.

Cell Transformation With Fluorescent Fusion Mammalian Expression Vectors

A fluorescent fusion protein containing GFP-LEDGF was generated with the Living Colors™ system (Clontech, Palo Alto, Calif.). The LEDGF cDNA containing the entire coding region was subcloned just downstream of the GFP gene (gene construct; pEGFP-LEDGF, protein product; GFP-LEDGF). We also generated another construct having the 5'-end 1600 nucleotides (N-terminus 130 amino acid). The HindIII-BamHI LEDGF cDNA fragment was subcloned just downstream of GFP gene (gene construct; pEFGP-mutLEDGF, protein product; GFP-mutLEDGF). Each of these constructs generated approximately a 90 kDa fusion protein (GFP-LEDGF) and a 45 kDa fusion protein (GFP-mutLEDGF) respectively. Expression of these constructs was driven by the cytomegalovirus late promoter. Fluorescence photography was performed with an Eclipse E600 microscope (Nikon, Melville, N.Y.).

Trypan Blue Dye Exclusion Test

The LECs in the 24-well tissue culture plates were incubated for 1–3 days in DMEM, with or without 10% FCS and anti-LEDGF Abs (Dilution 1:100). The Abs to LEDGF were prepared in rabbit. Two sets of controls were used: one consisted of the standard DMEM and the second contained normal rabbit serum in DMEM. LECs were trypsinized after incubation with the Abs to LEDGF. We estimated the number of viable cells in each suspension with a trypan blue dye (0.4% in saline, Gibco-BRL/LTI, Rockville, Md.) exclusion test, and calculated the percentage of damaged cells for each experiment.

Example 1

Cloning of LEDGF cDNA and Northern Analysis

Using sera of ARC patients we identified a clone (HLC10) from a human LEC cDNA expression library. The serun contained an Ab which bound to a protein produced by HLC10. Sequence analysis of the full length cDNA (SEQ ID NO:1) revealed an open reading frame able to encode a protein of 530 amino acids (SEQ ID NO:2) with a predicted molecular mass of 61 kDa. A BLAST database search revealed homology to the hepatoma-derived growth factor (HDGF—SEQ ID NOs:14 and 15) (Nakamura et al., *J. Biol. Chem.* 269:25143–25149, 1994). We thus named this gene LEDGF for lens-epithelial cell derived growth factor. The highest sequence homology between LEDGF and HDGF was found at the N-terminus.

Although, no signal peptide was found in LEDGF, there were several functional consensus sequences, two nucleotide localization consensus sequences, several putative case in kinase II sites, an A-kinase site, and two putative glycation sites. Forty-two percent of the amino acid residues of LEDGF were charged residues—24% negatively (aspartic acid and glutamic acid), and 18% positively (lysine, arginine, and histidine). The unusually high content of arginine and lysine suggests that this protein is unstable and susceptible to proteolytic cleavage. The secondary conformation of the molecule, predicted from its primary amino acid sequence, was predominantly P-sheets and turns according to the algorithm (Chou and Fasman, *Adv. Enzymol.* 47:45–148, 1978). The deduced amino acid sequence was validated by Ab binding studies. Using the deduced amino acid sequence of LEDGF as a guide, two oligopeptides were synthesized; one corresponding to the highly conserved site in the N-terminus (FFGTHETAFLGPKDIFPYSE; SEQ ID NO:4) and the second to a specific site in the C-terminus (LYNKFKNMFLVGEGDSVIT; SEQ ID NO:6). Abs to each peptide were then raised in rabbits. Both anti-LEDGF Abs (N-terminal and C-terminal) bound to a protein with a molecular weight of 61 kDa in human and mouse LECs. In addition, both Abs bound to LEDGF expressed in an *E. coli* expression system (see below and FIG. 1B, lane D). From these studies, we concluded that the clone which we had isolated was encoded to a 61 kDa protein expressed in human LECs.

Example 2

Tissue Specificity of LEDGF

We wished to know also which cell types expressed LEDGF. Total mRNAs were extracted from various mouse tissues, and Northern blot analysis indicated that mRNA corresponding to LEDGF was present at high levels in liver, lymphocytes and LECs and at low levels in many other tissues. When the Northern blots were washed at low stringency (0.5×SSC at 20° C.), we found two additional bands of molecular size 4.5 kbp and 2.7 kbp in the liver preparation. When washed at higher stringency (0.1×SSC at 62° C.), however, these bands disappeared, and only a 3.4 kbp band remained. This result suggested that mRNAs similar to LEDGF mRNA must be present in liver.

Next we detected LEDGF in cultured mouse and human LECs. Using a preparation of total soluble proteins, protein blot analysis, an ELISA assay, and the two afore-mentioned Ab probes (Abs to the N-terminus and C-terminus of LEDGF), we determined ELISA titers of ≧22,000 OD$_{492}$ units for each anti-LEDGF Ab. These Abs bound specifically to a 61 kDa protein in cultured LECs. In addition, four smaller bands (50, 45, 32, and 20 kDa proteins) were present on the protein blots. We also looked for LEDGF in capsulotomy specimens obtained at routine surgery for ARC, and in contrast to the results with cultured LECs, we found multiple blurry bands near the 61 kDa protein and no binding to the four smaller bands (50, 45, 32, and 20 kDa proteins). These results suggested that the 61 kDa protein was full-sized LEDGF, and the three smaller bands were partially degraded products. The multiple blurry bands near the 61 kDa protein in the capsulotomy specimens may be post-translationally modified, but not degraded LEDGF (see below and FIG. 4, lane 8). In the protein blot of liver there was a major band with a molecular weight about 35 kDa which must be HDGF. HDGF should cross-react with Abs to the N-terminus, but not the C-terminus peptide of LEDGF. Proteins with molecular weights similar to HDGF were found in lymphocytes, spleen, and lung cells. In addition, several positive bands were found in proteins of other tissues. Further work will be needed to determine if these proteins are partially degraded LEDGF, a family of similar proteins, or another group of proteins.

Example 3

Immunohistochemistry

Immunohistochemical staining for LEDGF on human LECs was carried out with light microscope and anti-LEDGF Abs (N-terminus) and horseradish peroxidase (HRP)-labeled secondary Abs. The entire cell surface was strongly stained with the Abs. The result suggested that LEDGF was bound to the cell surface of the LECs. Similarly, immunostaining of human LECs of capsulotomy specimens from cataract surgery exhibited strong positive staining.

Example 4

LEDGF is a Phospho-protein

We found several putative casein kinase II sites (see above) in LEDGF and also multiple blurry bands on the protein blot analysis of LEDGF from cultured LECs and from capsulotomy specimens. We speculated that LEDGF was a phosphorylated protein. We incubated mouse LECs which over-expressed LEDGF or the control LECs-vector (see below) with $^{32}$P-orhophosphate. Soluble proteins were immune-precipitated with anti-LEDGF Abs (mixture of N-terminal and C-terminal), the precipitated proteins were separated on SDS-PAGE and tested for radioisotope incorporation into LEDGF. As expected, the LEDGF (61 kDa-protein) was indeed phosphorylated (data not shown). Anti-LEDGF-Abs (mixture) preincubated with a mixture of N-terminal and C-terminal peptides did not precipitate 61 kDa phospho-protein (LEDGF).

Example 5

Expression of LEDGF in an *E. coli* Expression System

LEDGF cDNA was introduced into the bacterial expression system, glutathione-S-transferase (GST) gene fusion system (pGEX-2T), to facilitate LEDGF expression. The entire coding sequence of the cDNA was subcloned into pGEX-2T vector using SmaI and EcoRI sites. These expression systems produced very small amounts of full-size LEDGF. Since there was a highly GC rich sequence in the 5'-noncoding sequence of LEDGF mRNA, we removed the entire 5'-noncoding region by cutting at the BamHI site located just upstream of the initiation codon AUG. The LEDGF cDNA fragment was re-ligated directly under the GST. This construct produced a larger amount of a fusion protein (90 kDa) between GST (29 kDa), and L*EDGF* (61 kDa) in an *E. coli* strain (BL 21) (see FIG. 1B, lane D). We cleaved off GST molecule with thrombin protease, purified LEDGF, and used it for biological assays.

Example 6

LEDGF Stimulates Growth of LECs

To study the in vitro effects of LEDGF we expressed LEDGF in the *E. coli* expression system (pGEX-2T), and in mouse LECs. Various amounts of purified LEDGF (0.12–5 mg/ml) were added to the culture medium, and the growth of LECs was studied. Higher the concentrations of LEDGF (1–5 mg/ml), stimulated LEC growth ($^3$H-thymidine uptake) more, and lower concentrations (0.12–0.25 mg), stimulated LEC growth less (Table I). Suboptimal concentration of LEDGF for mouse LECs were 1–5 mg/ml for 2 days culture and 0.5–1.0 mg/ml for 3 days culture.

Example 7

Cells Over-expressing LEDGF Stimulate Growth

Mouse LECs and COS7 cells were transfected with the eukaryotic expression vector (pcDNA3) containing LEDGF cDNA. Cells were cultured in DMEM having 400 mg/ml of geneticin (a neomycin analog) for several weeks to establish a stable transfected cell line. The amount of LEDGF in transfected mouse LECs was more than 5–10 times higher than that in control cells (data not shown). Stable mouse LEC lines were established, then elicited ($1 \times 10^5$ cells/tube), frozen, and stored at $-70°$ C. These LECs are called "LECs-over expressing LEDGF", and the control LEC having an original vector are called "LECs-vector" in this paper.

After inoculation, LECs which overexpressed LEDGF attached themselves to the bottom of the culture plates much faster than those which expressed the LECs-vector. Growth of the LECs-over expressing LEDGF, as indicated by uptake of $^3$H-thymidine, was also much faster than that of the LECs-vector (Table II). Also, attachment of cells to the bottom of the culture plate after inoculation was much faster in COS7 cells which expressed LEDGF than in the COS7 cells containing only the vector. Growth of the COS7 cells-over expressing LEDGF was three times faster than that of the COS7-vector.

Next, we wished to know whether LEDGF regulated synthesis of specific proteins in LECs. We cultured mouse LECs over-expressing LEDGF and LECs-vector with $^{35}$S-methionine for 12 hrs. The soluble proteins were applied on the SDS-PAGE. The resulting autoradiogram indicated that synthesis of several (>7) proteins was stimulated in the LECs over-expressing LEDGF, and synthesis of two proteins was decreased (FIG. 1A). These results indicated that LEDGF regulates the synthesis and accumulation of several proteins in mouse LECs.

Example 8

LEDGF is Secreted Into Culture Medium

We wished to know whether the LEDGF was secreted from LECs and released into the culture medium. The mouse LECs-over expressing LEDGF and LECs-vector were cultured in DMEM without FCS. Initially mouse LECs were cultured in normal DMEM with 10% FCS for 1 day; after 1 day most LECs were attached to the bottom of culture plate. Then the initial medium was discarded, and the LECs were washed in DMEM without FCS. The medium was changed again after 12 hr incubation; then cells were cultured continuously for the next 3 days in DMEM without FCS. The medium was collected and called "conditioned medium". Almost all of cells appeared normal, but mouse LECs did grow a little in DMEM without FCS. The medium was harvested and applied to a Centricon 30 (Bio-con) which removed molecules smaller than 30 kDa. Protein blot analysis using anti-LEDGF Abs (mixtures) revealed a band of immune-positive 61 kDa protein LEDGF) (FIG. 1B). The yield of LEDGF from 50 ml of culture medium was approximately 0.6 mg/$4 \times 10^6$ cells/3 days. The result suggested that LEDGF was a secretory protein released from LECs into the culture medium. Similarly, COS7 cells-over expressing LEDGF were cultured in DMEM for 3 days, and we collected similarly conditioned medium. The amount of LEDGF in the medium was less (02 mg/$4 \times 10^6$ cells/3 days) than that in medium in which LECs had been cultured.

Figure 2:
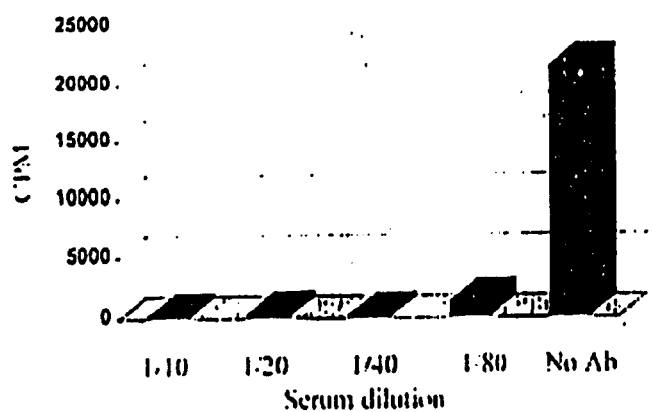
FIG. 2 shows the growth stimulating effects of LEDGF-conditioned medium on LECs.
Figure 2:
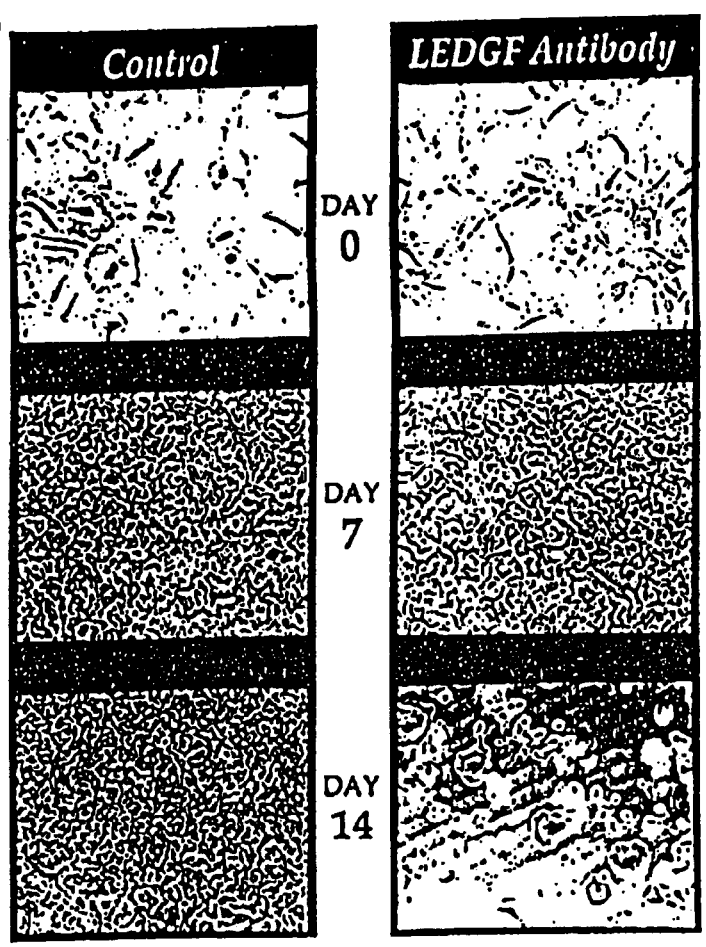

Next we examined the effect of conditioned medium obtained from COS7 cells over-expressing LEDGF on the growth of mouse LECs. The growth of cultured cells was stimulated 3-fold by the conditioned medium from COS7 cells-over expressing LEDGF compared to the conditioned medium from COS7 cells-vector. The latter did not stimulate LEC growth at all (FIG. 2). The stimulatory effect of the conditioned medium from COS7 cells-over expressing LEDGF was blocked by the addition of anti-LEDGF Abs. These results indicated that LEDGF from COS7 as well as LECs can stimulate LEC growth. Thus, we conclude that the LEDGF is a novel growth factor that is also secreted from various tissues.

Example 9

Anti-LEDGF Abs Killed LECs in Culture

We cultured mouse LECs in DMEM with 10% FCS to test whether anti-LEDGF Abs have an effect on the LECs. After two and half days of culture with the Abs, $^3$H-thymidine was added to the culture medium and the incubation continued for an additional 16 hrs. The cells were harvested, and radioisotope incorporation into DNA was investigated. Uptake of $^3$H-thymidine into LECs was inhibited significantly in the presence of anti-LEDGF Abs (1:10–1:80 dilutions) (FIG. 3A). In contrast, $^3$H-thymidine uptake in LECs cultured in the absence of the Abs was apparently stimulated. This result indicated that anti-LEDGF Abs strongly inhibited mitotic activity by the 3rd day in culture. Next we studied morphological changes of LECs cultured with the Abs. Human LECs were cultured for 14 days, with and without anti-LEDGF Ab (N-terminal) which had been purified by protein-A column chromatography. For the first 6 days LECs with and without Abs grew well, but, by the 7th day, a large numbers of cells incubated with anti-LEDGF Abs manifested damage, and by the 14th day most cells incubated with the Ab were dead and floated to the surface of the culture medium. The control cells incubated with serum collected from the rabbit before immunization with LEDGF, grew normally throughout the 14 day period (FIG. 3B).

Mouse LECs cultured in a similar fashion with and without anti-LEDGF Abs (C-terminal) or anti-LEDGF Abs (N-terminal) grew normally for 3 days, but by the 4–5th day, the cells cultured with either anti-LEDOGF Ab (C-terminal and N-terminal) appeared damaged. By 7 days, most of them were dead. Mouse LECs, cultured with control serum (pre-bled rabbit sera), grew continuously for the next 10 days. These experiments suggested that anti-LEDGF Abs block the stimulatory effect on cell growth by LEDGF, and that without such LEDGF stimulation, cells die.

Example 10

High Levels of Anti-LEDGF Ab are Present in Sera of Patients With ARC

Figure 4:
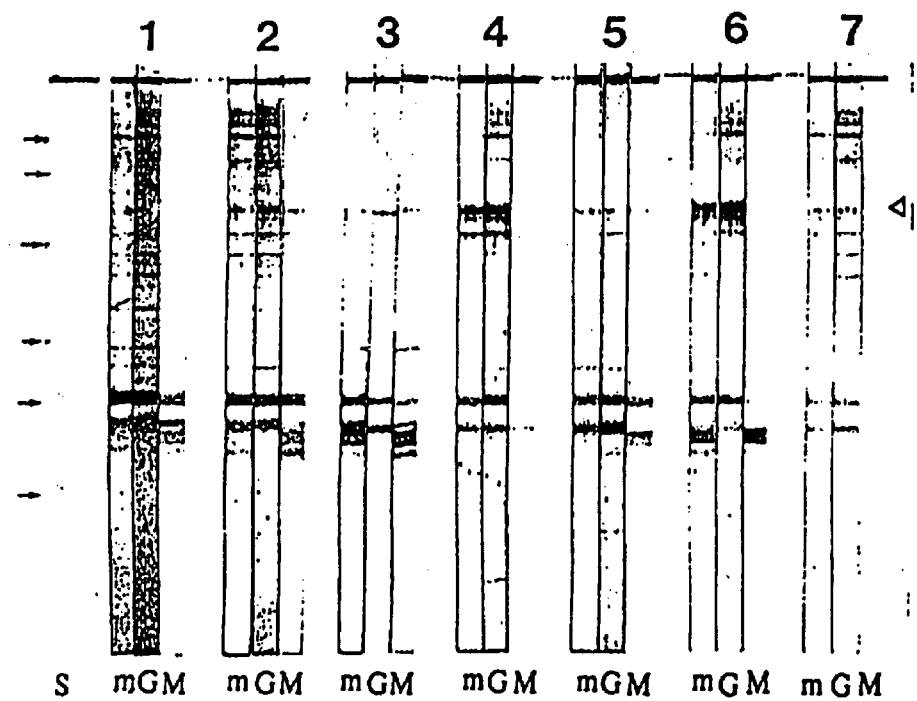
FIG. 4 shows the presence of anti-LEDGF Abs in patients with cataracts.

Since the clone (HLC10) was identified with serum from a patient with ARC, we expected to find auto-Abs to LEDGF in human serum. To confirm this, we performed protein blot analyses with human LEC proteins and sera from patients with ARC (FIG. 4). One hundred forty seven out of 153 sera from ARC patients had auto-Abs to LEDGF. These sera were strongly growth inhibitory for LECs in culture as shown previously, (Singh et al., *Exp. Eye Res.* Submitted, 1997). Both IgG and IgM were found in most sera from ARC patients (FIG. 4) and IgM was more 19 times more cytotoxic than IgG on a per mg protein basis.

Example 11

Temperature Effect on LECs Over-expressing GFP-LEDGF 50,000 LECs were cultured on (triplicate) 24-well culture plates in 0.5 ml of DMEM containing 10% FCS and were incubated overnight at 37° C. Most cells were attached on the bottom of plates after 24 hrs. The cells were then washed twice with 0.5 ml of DMEM without FCS and were kept in culture for additional 7 days at 41° C. in the DMEM . The initial cell number/well on the plate was about the same between cells over-expressing LEDGF and the controls. After 1 day, LECs over-expressing LEDGF survived well (>78% cells) and grew further. By the 3rd day cell growth appeared to reach a plateau, and between days 3–7 cells did not grow but in their majority survived (83% at 3 days and 72% at 7 days) the serum free medium at 41° C. In contrast, control cells grew and survived well during the first 24 hrs (>80% survival), but gradually started dying after that (59% survival at 3 days and 39% survival at 7 days). These results show that LECs over-expressing LEDGF survive better under heat-stress.

Example 12

Expression of Specific Proteins in the Cells Over-expressing LEDG

LECs over-expressing GFP-LEDGF and control LECs (transfected with vector alone-GFP plasmid) were cultured at 37° C. for 2 days. Total cell homogenates from each cell type were prepared after the 2 day culture. Equal amounts of proteins were separated on tan SDS-PAGE and blotted onto membrane filters for immunostaining with corresponding Abs. We quantified Heat Shock Proteins (HSPs) 100, 90, 70, 60, 27, and αβ-crystallin on the blot using antibody probes (Gibco-BRL). Although, HSP 60 was expressed at relatively high levels, it was not stimulated in LECs overexpressing LEDGF. We found between 10 and 5 times higher levels of HSP 27 and αβ-crystallin, respectively, in these cells over-expressing LEDGF than that in the control cells having vector alone. The rest of HSPs (100, 90, 70, and 32) were not expressed at a detectable level in LECs with or without over-expressing LEDGF.

Example 13

Oxidative Stress on LECs Over-expressing LEDGF

A well-studied environmental stress condition in the lens field is a oxidation. We investigated whether LECs resisted oxidative stress damage. The LECs were cultured in the DMEM with 10% FCS for 1 day as described above. Cells were then transferred into serum free DMEM in the presence of various amounts of $H_2O_2$ (from 31 $\mu$M to 250 $\mu$M). Growth and survival of LECs were monitored under the light microscope. The LECs over-expressing LEDGF grew and survived better than the cells being transfected with the vector alone. At 125 and 62.5 $\mu$M of $H_2O_2$, the control cells were mostly dead after a 6 hour incubation, but the cells over-expressing LEDGF survived much better (>80% survival). At 62.5 $\mu$M of H202, control cells were mostly dead after a 24 hr incubation with the LECs over-expressing LEDGF surviving better (>80% survival).

Figure Legends

FIG. 1. In vitro effects from LEDGF over-expression on LECs.

(A). Mouse LECs over-expressing LEDGF (lane B) and LECs-vector (lane A) were cultured for 2.5 days, then $^{35}$S-methionine was incorporated for 12 hrs. Protein synthesis of LECs over-expressing LEDGF was apparently altered. The synthesis of some proteins was stimulated (indicated by arrow in the right margin) and of others was inhibited (indicated by arrow in the left margin). Equal amounts of radioisotope was applied in these two samples.

(B). LEDGF was found in culture medium. Mouse LECs-over expressing LEDGF or COS7-over expressing LEDGF were cultured in DMEM for 72 hrs, and LEDGF in the medium was analyzed by immunostaining with Abs to LEDGF. Lane A, Molecular size markers are the same as on FIG. 2B. Lane B, LEDGF in medium from cultured COS7 cells-over expressing LEDGF. Lane C, LEDGF in medium from cultured mouse LEC-over expressing LEDGF. Lane D, *Expression of LEDGF in prokaryotic pGEX*-2T expression vector system (*E. coli*, BL21). Fusion protein (100 kDa) between LEDGF and GST is indicated by an arrow head in the right margin. LEDGF is indicated by an arrow in the left margin.

FIG. 2. Growth stimulating effects of LEDGF-conditioned medium on LECs. Conditioned medium from COS7 cells over-expressing LEDGF stimulated $^3$H-thymidine uptake in mouse LECs. +LEDGF indicates that conditioned medium from COS7 cells over-expressing LEDGF. −LEDGF and DMEM indicate conditioned medium from COS7 vector-alone and medium only, respectively, showing no significant growth stimulation. +LEDGF+Abs indicates that the conditioned medium from COS7 over-expressing LEDGF mixed with equal molar amounts of Abs to LEDGF. This preparation did not stimulate $^3$H-thymidine incorporation.

Figure 3:
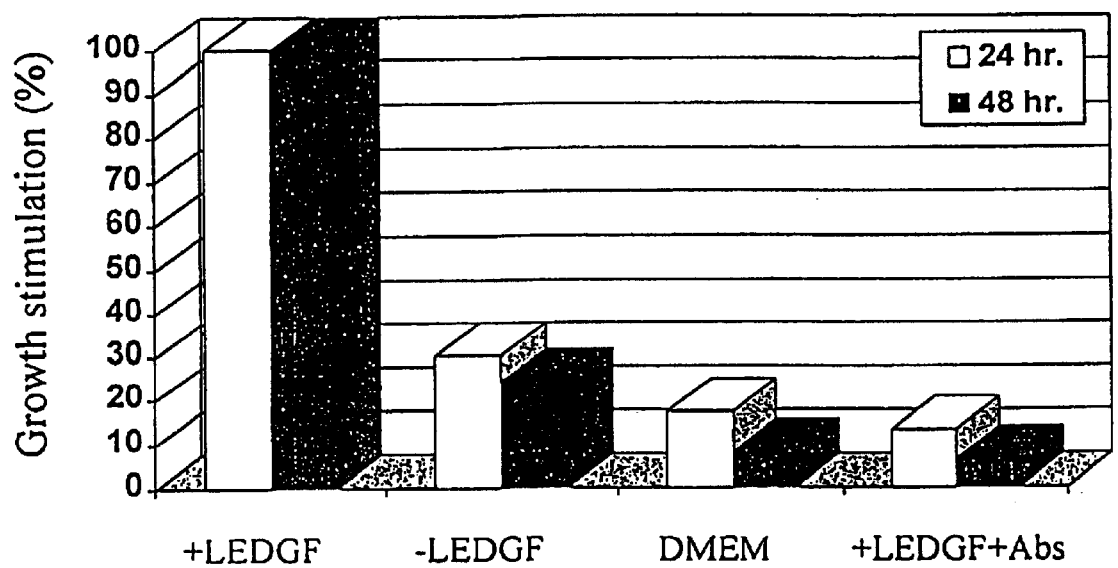
FIG. 3 shows the in vitro anti-LEDGF Ab effects on LECs.

FIG. 3. In vitro anti-LEDGF Ab effects on LECs.

(A). The Abs to LEDGF inhibited $^3$H-thymidine uptake in mouse LECs in culture. The LECs were cultured for 2.5 days with 1:10–1:80 dilutions of Ab to LEDGF, then $^3$H-thymidine was added, and further incubated an additional 16 hrs. The incorporated radioisotope (CPM) was analyzed in a scintillation counter. The experiment was triplicated and presented as average CPMs.

(B). Human LECs killed by Abs to LEDGF. Human LECs were cultured +/− Abs to LEDGF. After 7 days in culture, the cell number decreased, and almost all LECs in cultures with Abs to LEDGF died. Control cultures without anti-LEDGF Abs grew normally.

FIG. 4. Presence of anti-LEDGF Abs in sera of cataract patients. Proteins obtained from human capsulotomy specimens were each blotted on 2 mm wide millipore filters, and each filter was stained with serum from individuals with ARC. Approximately 1 mg/well of protein was analyzed, and each serum was diluted 1:20. An arrow indicates the 61 kDa region, and the nearby multiple fuzzy bands. Sera from 7 patients (numbered 1–7 at the top) are presented. The codes are for a second Ab or Ab mixture: goat anti-human IgA, IgG, or IgM. m: IgA+IgG+IgM mixture; G:IgG; M:IgM; S:size markers (108, 80, 51, 34, 27, and 16 kDa). Some sera have predominantly IgG and others have predominantly IgM. Lane 1 represents a patient with ARC had no detectable level of Ab to LEDGF, the rest of patients (lane 2–7) had the Abs. Lane 8 was presented as a reference. The same protein blot was stained with rabbit Abs to LEDGF (N-terminal, SEQ ID NO:4) and goat anti-rabbit IgG was used as a the second Ab. Note the fuzzy bands in the 61 kDa region (arrow). Approximately 1 μg/well of protein was analyzed with the human sera or Ab to LEDGF. Goat anti-human or anti-rabbit IgG were used as the second Abs.

FIG. 5. A kit comprising an agent of the invention (e.g., anti-LEDGF Abs, LEDGF epitopes, etc.), a control agent, and instructions for utilizing such agents in diagnostic or therapeutic applications.

TABLE I

Effect of recombinant LEDGF on $^3$H-thymidine uptake of LECs in culture

| Incubation time (day) Concentration of LEDGF | $^3$H-thymidine uptake (cpm) | | | | | |
|---|---|---|---|---|---|---|
| (mg/well) | 5 | 1 | 0.5 | 0.25 | 0.12 | 0.00 |
| 2 | 57,030 ± 2,400 | 54,500 ± 3,400 | 53,000 ± 2,600 | 38,900 ± 2,760 | NA | 34,000 ± 2,300 |
| 3 | 74,700 ± 1,300 | 101,950 ± 5,600 | 97,400 ± 1,500 | 90,300 ± 4,900 | 85,200 ± 4,400 | 47,400 ± 4,600 |

Equal numbers of mouse LECs (1×10$^5$ cells/well) were inoculated in the flat bottom microtiter plates and incubated for 2–3 days with 5,1, 0.5, 0.25, 0.12 and 0.00 LEDGF. Three wells of mouse LECs were cultured for one experiment. The date represents an average of three experiments. Radioisotope was incorporated for 16 hours with 1 μCi/well of $^3$H-thymidine.

TABLE II

Over expressed LEDGF stimulates $^3$H-thymidine uptake in mouse LECs

| Incubation Time (day) | Mouse LECs with LEDGF pcDNA3 | Mouse LECs with Control pcDNA3 |
|---|---|---|
| 1 | 38,243 ± 1,873 | 7,694 ± 209 |
| 2 | 110,671 ± 3,251 | 24,223 ± 2,449 |
| 3 | 277,276 ± 26,324 | 47,909 ± 3,514 |
| 4 | 213,754 ± 13,874 | 106,160 ± 8,383 |
| 5 | 244,208 ± 14,252 | 103,810 ± 8,100 |
| 6 | 74,812 ± 8,005 | 119,385 ± 8,310 |

Equal numbers of mouse LECs (1×10$^5$ cells/well) were inoculated in the flat bottom microtiter plates. Three wells of mouse LECs were cultured for each experiment. Data are an average of three experiments. Radioisotope was incorporated for 16 hours with 1 μCi/well of $^3$H-thymidine. Mouse LECs became confluent after 5 days in culture, and uptake of $^3$H-thymidine declined by 6 days.

TABLE III

Sequences with partial homologies to LEDGF

Sequences with GenBank accession numbers:

U94319, U21717, Z78418, U58334, M21096, Z68750, X66367, M64437, AB014549, M73529, U48436,
AF020200, Y07662, D82352, Z78205, U92436, X69910, AC004781, M24603, U56440, X02596, U62542,
M95497, L16683, AJ002310, M95603, X94677, AF000993, AJ000109, AF012603, S37093, X76217,
D83652, X66223, D86982, X54806, AL031031, M72711, U85962, U10564, M97563, S70397, AF039840,
U59322, U92437, U97663, AB001835, S69350, U00674, U31809, M15025, Y00661, D83206, U63894,
X56465, X66096, M64344, U91679, AF020199, M83298, X52828, U96180, M80550, AF000992,
AJ002308, L76569, U58678, U49791, U30246, U19759, AA773624, AA521322, AA228130, AA772105,
AA285372, N41025, W19666, AA937940, AA767142, N40993, N48306, N22081, D51131, AA679749,
AA490641, AA115344, AA515178, AA227982, AA679542, N50725, AA639697, AA761805, AA906700,
AA102786, AA322886, AA788615, C02698, C05293, H68589, H05226, AA456657, AA758913, D82424,
N49031, A648034, T24523, N47125, N64617, AA393305, AA861341, AA992385, AA389644,
AA758341, N75869, R18910, AA626371, AA465159, AA368664, D81382, H86544, H84298, AA644639,
AA877813, AA011028, AA056275, AA018441, N53694, AA020992, T83201, AA058563, AA047220,
H86126, N41507, W20450, AA169778, AA731406, R38845, AA731403, AA770198, AA968479, R28454,
R22429, D62104, AA250931, AA488229, H97847, AA283145, AA169696, H82607, AI041041, AA608413,
AA867331, AA921107, AI048060, AA184165, AA039116, AA718349, AA542188, AA591351, AA177775,
AA692690, AA146201, AA867019, AA792020, AA170751, AA693092, AA656644, AA636419,
AA271872, AA146236, AA177309, AA623881, AA672210, AA940100, AA693167, AA681870, W83156,
AA124286, AA547043, AA120067, AA647991, AA623726, AA014322, AA213040, AA511225,
AA960457, AA213201, AA170671, AI035693, AA162694, AA444251, AA516678, AA023755, AA110235,
AA407127, AA855403, AA050131, AA619989, AA073118, AA161809, AA222163, AA871188,
AA792147, A796131, AA110787, AA710005, AA710374, AA517361, AA537432, AA718233,
AA870039, AA111345, W08033, AA260016, W99877, AA655390, D18351, AA072736, AA119746,
AA407292, AA645669, AA674540, AA015354, W54255, AA106100, AA114708, AA546945, AA574627,
AA756108, AA764184, Z74644, AA771131, AA013681, AA110312, AA686890, H34999, AA964144,
AI045732, AA392351, C41181, D48746, AI011500, C41350, D67725, C40685, D74054, D74250, C45006,
AA216474, H16500, R65140, D47814, W51610, AA728013, AA592046, AA294717, AA228197,
AA257749, W51555, AA275402, AA791301, AA728017, AA0007746, AA542770, AA257821,
AA294785, W69065, AA114525, AA241702, AA539267, R65141, AA216511, R65147, H21271,
AA542704, N52099, AA728000, AA072531, AA294198, AA956969, AA964324, AA998070, AA955499,
H74375, AA550426, AA858784, AA963079, D24013, AI011491, AI028970, AA859961, N97602,
AA799744, AA817741, AA440741, AA944662, AI029487, C74424, AA965055, D23620, D16039, R86636,
C26690, C73046, AA851680, AA851681, AA957337, D49269, AA957771, AA997712, AI029018, D24530,
D24454, R90424, C11742, AI008716, AI012646, D24476, C19142, C19898, C74483, AA728663,
AI030304, D23783.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is presented below and is followed by a sequence listing:

---

We claim:

1. An isolated nucleic acid molecule selected from the group consisting of:
   (a) a nucleic acid molecule that comprises SEQ ID NO:1,
   (b) a nucleic acid molecule that comprises SEQ ID NO:13,
   (c) nucleic acid molecules that differ from the nucleic acid molecules of (a) in codon sequence due to the degeneracy of the genetic code, and
   (d) complements of (a), (b), or (c).

2. The isolated nucleic acid molecule of claim 1, wherein the isolated nucleic acid molecule comprises SEQ ID NO:1.

3. The isolated nucleic acid molecule of claim 1, wherein the isolated nucleic acid molecule is the nucleic acid molecule of SEQ ID NO:13.

4. An expression vector comprising the isolated nucleic acid molecule of claim 3 operably linked to a promoter.

5. A host cell transformed or transfected with the expression vector of claim 4.

6. An expression vector comprising the isolated nucleic acid molecule of claim 1 operably linked to a promoter.

7. A host cell transformed or transfected with the expression vector of claim 6.

8. A kit comprising a package, wherein the package contains:
   (i) a nucleic acid agent selected from the group consisting of:
      (a) a nucleic acid molecule which hybridizes under stringent conditions to a molecule consisting of the nucleic acid of SEQ ID NO:1 and which codes for a polypeptide that stimulates the growth of lens epithelial cells, wherein the stringent conditions comprise hybridization at 65° C. in hybridization buffer wherein the hybridization buffer comprises 3.5× SSC, 0.02% Ficoll, 0.02% polyvinyl pyrolidone, 0.02% Bovine Serum Albumin, 2.5 mM $NaH_2PO_4$ (pH7), 0.5% SDS, and 2 mM EDTA,
      (b) nucleic acid molecules that differ from the nucleic acid molecules of (a) in codon sequence due to the degeneracy of the genetic code, and
      (c) complements of (a) or (b), and
   (ii) a control comprising an isolated nucleic acid of claim 1.

\* \* \* \* \*

SEQUENCE LISTING

<160> NUMBER OF SEQ ID NOS: 22

<210> SEQ ID NO 1
<211> LENGTH: 3360
<212> TYPE: DNA
<213> ORGANISM: Homo Sapiens
<220> FEATURE:
<221> NAME/KEY: CDS
<222> LOCATION: (311)...(1900)

<400> SEQUENCE: 1

```
gggagccgcg cgggagcagc gcagctacgg cggcggcagc ggcggcgcgg ttgcgattcc      60
gagccgttga gacgcctctg cggcagctgg tggcgcaggt ggcttgcgtg gacgcgggta     120
gaggcgaccg gccagcaacc gcagcgtcgg cgcccgcggc cccggcagca ggcgcgtcgg     180
gacgccccga ggcatcctcc cccgcccgcg ggcccggtag ctgggcccgc gtccgccgcc     240
cgcatccccg cgccgccgca tctcctcgcc gcctcccggg cttcggaccc ccggtctcgc     300
```

-continued

```
ccccggaaac atg act cgc gat ttc aaa cct gga gac ctc atc ttc gcc          349
            Met Thr Arg Asp Phe Lys Pro Gly Asp Leu Ile Phe Ala
             1               5                  10 aag atg aaa ggt tat ccc cat tgg cca gct cga gta gac gaa gtt cct          397
Lys Met Lys Gly Tyr Pro His Trp Pro Ala Arg Val Asp Glu Val Pro
 15              20                  25 gat gga gct gta aag cca ccc aca aac aaa cta ccc att ttc ttt ttt          445
Asp Gly Ala Val Lys Pro Pro Thr Asn Lys Leu Pro Ile Phe Phe Phe
 30              35                  40                  45 gga act cat gag act gct ttt tta gga cca aag gat ata ttt cct tac          493
Gly Thr His Glu Thr Ala Phe Leu Gly Pro Lys Asp Ile Phe Pro Tyr
                 50                  55                  60 tca gaa aat aag gaa aag tat ggc aaa cca aat aaa aga aaa ggt ttt          541
Ser Glu Asn Lys Glu Lys Tyr Gly Lys Pro Asn Lys Arg Lys Gly Phe
             65                  70                  75 aat gaa ggt tta tgg gag ata gat aac aat cca aaa gtg aaa ttt tca          589
Asn Glu Gly Leu Trp Glu Ile Asp Asn Asn Pro Lys Val Lys Phe Ser
         80                  85                  90 agt caa cag gca gca act aaa caa tca aat gca tca tct gat gtt gaa          637
Ser Gln Gln Ala Ala Thr Lys Gln Ser Asn Ala Ser Ser Asp Val Glu
     95                  100                 105 gtt gaa gaa aag gaa act agt gtt tca aag gaa gat acc gac cat gaa          685
Val Glu Glu Lys Glu Thr Ser Val Ser Lys Glu Asp Thr Asp His Glu
110                 115                 120                 125 gaa aaa gcc agc aat gag gat gtg act aaa gca gtt gac ata act act          733
Glu Lys Ala Ser Asn Glu Asp Val Thr Lys Ala Val Asp Ile Thr Thr
                 130                 135                 140 cca aaa gct gcc aga agg ggg aga aag aga aag gca gaa aaa caa gta          781
Pro Lys Ala Ala Arg Arg Gly Arg Lys Arg Lys Ala Glu Lys Gln Val
             145                 150                 155 gaa act gag gag gca gga gta gtg aca aca gca aca gca tct gtt aat          829
Glu Thr Glu Glu Ala Gly Val Val Thr Thr Ala Thr Ala Ser Val Asn
         160                 165                 170 cta aaa gtg agt cct aaa aga gga cga cct gca gct aca gaa gtc aag          877
Leu Lys Val Ser Pro Lys Arg Gly Arg Pro Ala Ala Thr Glu Val Lys
     175                 180                 185 att cca aaa cca aga ggc aga ccc aaa atg gta aaa cag ccc tgt cct          925
Ile Pro Lys Pro Arg Gly Arg Pro Lys Met Val Lys Gln Pro Cys Pro
190                 195                 200                 205 tca gag agt gac atc att act gaa gag gac aaa agt aag aaa aag ggg          973
Ser Glu Ser Asp Ile Ile Thr Glu Glu Asp Lys Ser Lys Lys Lys Gly
                 210                 215                 220 caa gag gaa aaa caa cct aaa aag cag cct aag aag gat gaa gag ggc         1021
Gln Glu Glu Lys Gln Pro Lys Lys Gln Pro Lys Lys Asp Glu Glu Gly
             225                 230                 235 cag aag gaa gaa gat aag cca aga aaa gag ccg gat aaa aaa gag ggg         1069
Gln Lys Glu Glu Asp Lys Pro Arg Lys Glu Pro Asp Lys Lys Glu Gly
         240                 245                 250 aag aaa gaa gtt gaa tca aaa agg aaa aat tta gct aaa aca ggg gtt         1117
Lys Lys Glu Val Glu Ser Lys Arg Lys Asn Leu Ala Lys Thr Gly Val
     255                 260                 265 act tca acc tcc gat tct gaa gaa gaa gga gat gat caa gaa ggt gaa         1165
Thr Ser Thr Ser Asp Ser Glu Glu Glu Gly Asp Asp Gln Glu Gly Glu
270                 275                 280                 285 aag aag aga aaa ggt ggg agg aac ttt cag act gct cac aga agg aat         1213
Lys Lys Arg Lys Gly Gly Arg Asn Phe Gln Thr Ala His Arg Arg Asn
                 290                 295                 300 atg ctg aaa ggc caa cat gag aaa gaa gca gca gat cga aaa cgc aag         1261
Met Leu Lys Gly Gln His Glu Lys Glu Ala Ala Asp Arg Lys Arg Lys
```

-continued

|  | 305 |  |  |  | 310 |  |  |  | 315 |  |  |  |  |
|---|---|---|---|---|---|---|---|---|---|---|---|---|---|
| caa | gag | gaa | caa | atg | gaa | act | gag | cag | cag | aat | aaa | gat | gaa gga aag | 1309 |
| Gln | Glu | Glu | Gln | Met | Glu | Thr | Glu | Gln | Gln | Asn | Lys | Asp | Glu Gly Lys |
|  |  | 320 |  |  |  |  | 325 |  |  |  |  | 330 |  |

| aag | cca | gaa | gtt | aag | aaa | gtg | gag | aag | aag | cga | gaa | aca | tca atg gat | 1357 |
|---|---|---|---|---|---|---|---|---|---|---|---|---|---|---|
| Lys | Pro | Glu | Val | Lys | Lys | Val | Glu | Lys | Lys | Arg | Glu | Thr | Ser Met Asp |
|  | 335 |  |  |  |  | 340 |  |  |  |  | 345 |  |  |

| tct | cga | ctt | caa | agg | ata | cat | gct | gag | att | aaa | aat | tca | ctc aaa att | 1405 |
|---|---|---|---|---|---|---|---|---|---|---|---|---|---|---|
| Ser | Arg | Leu | Gln | Arg | Ile | His | Ala | Glu | Ile | Lys | Asn | Ser | Leu Lys Ile |
| 350 |  |  |  |  | 355 |  |  |  |  | 360 |  |  | 365 |

| gat | aat | ctt | gat | gtg | aac | aga | tgc | att | gag | gcc | ttg | gat | gaa ctt gct | 1453 |
|---|---|---|---|---|---|---|---|---|---|---|---|---|---|---|
| Asp | Asn | Leu | Asp | Val | Asn | Arg | Cys | Ile | Glu | Ala | Leu | Asp | Glu Leu Ala |
|  |  |  | 370 |  |  |  |  | 375 |  |  |  |  | 380 |

| tca | ctt | cag | gtc | aca | atg | caa | caa | gct | cag | aaa | cac | aca | gag atg att | 1501 |
|---|---|---|---|---|---|---|---|---|---|---|---|---|---|---|
| Ser | Leu | Gln | Val | Thr | Met | Gln | Gln | Ala | Gln | Lys | His | Thr | Glu Met Ile |
|  |  |  |  | 385 |  |  |  |  | 390 |  |  |  | 395 |

| act | aca | ctg | aaa | aaa | ata | cgg | cga | ttc | aaa | gtt | agt | cag | gta atc atg | 1549 |
|---|---|---|---|---|---|---|---|---|---|---|---|---|---|---|
| Thr | Thr | Leu | Lys | Lys | Ile | Arg | Arg | Phe | Lys | Val | Ser | Gln | Val Ile Met |
|  |  |  | 400 |  |  |  |  | 405 |  |  |  |  | 410 |

| gaa | aag | tct | aca | atg | ttg | tat | aac | aag | ttt | aag | aac | atg | ttc ttg gtt | 1597 |
|---|---|---|---|---|---|---|---|---|---|---|---|---|---|---|
| Glu | Lys | Ser | Thr | Met | Leu | Tyr | Asn | Lys | Phe | Lys | Asn | Met | Phe Leu Val |
|  | 415 |  |  |  |  | 420 |  |  |  |  | 425 |  |  |

| ggt | gaa | gga | gat | tcc | gtg | atc | acc | caa | gtg | ctg | aat | aaa | tct ctt gct | 1645 |
|---|---|---|---|---|---|---|---|---|---|---|---|---|---|---|
| Gly | Glu | Gly | Asp | Ser | Val | Ile | Thr | Gln | Val | Leu | Asn | Lys | Ser Leu Ala |
| 430 |  |  |  |  | 435 |  |  |  |  | 440 |  |  | 445 |

| gaa | caa | aga | cag | cat | gag | gaa | gcg | aat | aaa | acc | aaa | gat | caa ggg aag | 1693 |
|---|---|---|---|---|---|---|---|---|---|---|---|---|---|---|
| Glu | Gln | Arg | Gln | His | Glu | Glu | Ala | Asn | Lys | Thr | Lys | Asp | Gln Gly Lys |
|  |  |  |  | 450 |  |  |  |  | 455 |  |  |  | 460 |

| aaa | ggg | cca | aac | aaa | aag | cta | gag | aag | gaa | caa | aca | ggg | tca aag act | 1741 |
|---|---|---|---|---|---|---|---|---|---|---|---|---|---|---|
| Lys | Gly | Pro | Asn | Lys | Lys | Leu | Glu | Lys | Glu | Gln | Thr | Gly | Ser Lys Thr |
|  |  |  | 465 |  |  |  |  | 470 |  |  |  |  | 475 |

| cta | aat | gga | gga | tct | gat | gct | caa | gat | ggt | aat | cag | cca | caa cat aac | 1789 |
|---|---|---|---|---|---|---|---|---|---|---|---|---|---|---|
| Leu | Asn | Gly | Gly | Ser | Asp | Ala | Gln | Asp | Gly | Asn | Gln | Pro | Gln His Asn |
|  |  |  | 480 |  |  |  |  | 485 |  |  |  |  | 490 |

| ggg | gag | agc | aat | gaa | gac | agc | aaa | gac | aac | cat | gaa | gcc | agc acg aag | 1837 |
|---|---|---|---|---|---|---|---|---|---|---|---|---|---|---|
| Gly | Glu | Ser | Asn | Glu | Asp | Ser | Lys | Asp | Asn | His | Glu | Ala | Ser Thr Lys |
|  | 495 |  |  |  |  | 500 |  |  |  |  | 505 |  |  |

| aaa | aag | cca | tcc | agt | gaa | gag | aga | gag | act | gaa | ata | tct | ctg aag gat | 1885 |
|---|---|---|---|---|---|---|---|---|---|---|---|---|---|---|
| Lys | Lys | Pro | Ser | Ser | Glu | Glu | Arg | Glu | Thr | Glu | Ile | Ser | Leu Lys Asp |
| 510 |  |  |  |  | 515 |  |  |  |  | 520 |  |  | 525 |

| tct | aca | cta | gat | aac | taggttgaca | tacctggaat | atagagaaca | cttgagaagt | 1940 |
|---|---|---|---|---|---|---|---|---|---|
| Ser | Thr | Leu | Asp | Asn |  |  |  |  |  |
|  |  |  |  | 530 |  |  |  |  |  |

| ttgtaatggt | tttcatttga | aatagactgc | tggaagttta | aattttata | agcataggtt | 2000 |
|---|---|---|---|---|---|---|
| tgatgttgaa | aacttgtttt | gagggagaaa | atccctttgt | tttaaagtaa | agtaaacatt | 2060 |
| atcgctaagt | gtaacttgtg | cagtattaac | agctacatta | tacagtaaat | gtgggataaa | 2120 |
| atccatttag | aaaatgttaa | actgcttttc | cagacatggt | tgtagcatat | tttcaattag | 2180 |
| tgtgtgtatg | ttaatgtgta | attgatagta | gaacaaagtt | acattttaa | aactgctact | 2240 |
| tgtataaacc | ttgcctcttt | tcccaaatac | tgtgggtttt | gtgcatagtt | tttacaaacc | 2300 |
| ttggatttac | cagactgtct | tttcactgtt | tgtgggtttt | gtagaagtta | cacattttta | 2360 |
| tggtagataa | aatgttactt | ctatacaagt | actcactccc | ttttatcaa | aagttaattt | 2420 |
| taatctcaca | gtctcattg | tgctacatta | tccagcttct | ttggaacaat | gtgtgctctg | 2480 |
| tatggttttt | tttggtatga | caactaatta | agcaactgac | attgaactga | gaattctaca | 2540 |
| aactataaaa | cattaatttt | tgaaggtaat | ttagttttgt | ggctgggcat | tcagtgaagt | 2600 |

-continued

```
cttaggactt ctttgcagac aactgactgg gtatatatag gaatgaatct ggctttaggg    2660
ttaaatcatt taaggtcctt ttataggcag gcactagtaa ctaaaactga aaactaagta    2720
agtttatttt tgaggaatgt tgttaaaaat gtctttagga agtcactaaa acttaattgg    2780
aagaaaaaat catgatgctt atacaataaa tatgaataaa tgttatataa ggaaactcac    2840
ctatttgaaa tcatggctat attgttttta ttttctagat tccaaaaata caaacactag    2900
ttgttccagc attgtacttt gataagtctg tacattgacg tgtatggact aaatccaggg    2960
taaaatcaat gttacaaaat ttaagggtat gttaactaaa ggatagcatt tctaagatat    3020
tttgaatatt agggtcattt ggcacttctc agcaagtagg atacttctca tgttttttgaa    3080 attatatgaa tatggaaaaa aatggcttaa gaccagcgtc tctgtatgac attgtgtggt    3140
tgaccctctg agataactgt tttcatctac agaattgcat ttttgctttt aaagaggtct    3200
tataatggaa ctaggaatca ccgttttgag agaacctgca tatataccag tcattatctg    3260
tttggtcctt atacagtttt aacttactta gatttattct agttaagcca taagttcaac    3320
gtgtaaactt gttttcatta aagaattttt ctatcaaaaa                          3360
```

<210> SEQ ID NO 2
<211> LENGTH: 530
<212> TYPE: PRT
<213> ORGANISM: Homo Sapiens

<400> SEQUENCE: 2

```
Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205

Asp Ile Ile Thr Glu Glu Asp Lys Ser Lys Lys Lys Gly Gln Glu Glu
    210                 215                 220

Lys Gln Pro Lys Lys Gln Pro Lys Lys Asp Glu Glu Gly Gln Lys Glu
225                 230                 235                 240
```

-continued

```
Glu Asp Lys Pro Arg Lys Glu Pro Asp Lys Lys Glu Gly Lys Lys Glu
                245                 250                 255

Val Glu Ser Lys Arg Lys Asn Leu Ala Lys Thr Gly Val Thr Ser Thr
            260                 265                 270

Ser Asp Ser Glu Glu Glu Gly Asp Gln Glu Gly Glu Lys Lys Arg
        275                 280                 285

Lys Gly Gly Arg Asn Phe Gln Thr Ala His Arg Arg Asn Met Leu Lys
    290                 295                 300

Gly Gln His Glu Lys Glu Ala Ala Asp Arg Lys Arg Lys Gln Glu Glu
305                 310                 315                 320

Gln Met Glu Thr Glu Gln Gln Asn Lys Asp Glu Gly Lys Lys Pro Glu
            325                 330                 335

Val Lys Lys Val Glu Lys Arg Glu Thr Ser Met Asp Ser Arg Leu
        340                 345                 350

Gln Arg Ile His Ala Glu Ile Lys Asn Ser Leu Lys Ile Asp Asn Leu
        355                 360                 365

Asp Val Asn Arg Cys Ile Glu Ala Leu Asp Glu Leu Ala Ser Leu Gln
    370                 375                 380

Val Thr Met Gln Gln Ala Gln Lys His Thr Glu Met Ile Thr Thr Leu
385                 390                 395                 400

Lys Lys Ile Arg Arg Phe Lys Val Ser Gln Val Ile Met Glu Lys Ser
            405                 410                 415

Thr Met Leu Tyr Asn Lys Phe Lys Asn Met Phe Leu Val Gly Glu Gly
        420                 425                 430

Asp Ser Val Ile Thr Gln Val Leu Asn Lys Ser Leu Ala Glu Gln Arg
    435                 440                 445

Gln His Glu Glu Ala Asn Lys Thr Lys Asp Gln Gly Lys Lys Gly Pro
    450                 455                 460

Asn Lys Lys Leu Glu Lys Gln Thr Gly Ser Lys Thr Leu Asn Gly
465                 470                 475                 480

Gly Ser Asp Ala Gln Asp Gly Asn Gln Pro Gln His Asn Gly Glu Ser
            485                 490                 495

Asn Glu Asp Ser Lys Asp Asn His Glu Ala Ser Thr Lys Lys Pro
        500                 505                 510

Ser Ser Glu Glu Arg Glu Thr Glu Ile Ser Leu Lys Asp Ser Thr Leu
        515                 520                 525

Asp Asn
    530

<210> SEQ ID NO 3
<211> LENGTH: 57
<212> TYPE: DNA
<213> ORGANISM: Homo Sapiens
<220> FEATURE:
<221> NAME/KEY: CDS
<222> LOCATION: (1)...(57)

<400> SEQUENCE: 3 ttt ttt gga act cat gag act gct ttt tta gga cca aag gat ata ttt      48
Phe Phe Gly Thr His Glu Thr Ala Phe Leu Gly Pro Lys Asp Ile Phe
 1               5                  10                  15 cct tac tca                                                          57
Pro Tyr Ser

<210> SEQ ID NO 4
<211> LENGTH: 19
```

-continued

```
<212> TYPE: PRT
<213> ORGANISM: Homo Sapiens

<400> SEQUENCE: 4

Phe Phe Gly Thr His Glu Thr Ala Phe Leu Gly Pro Lys Asp Ile Phe
1               5                   10                  15

Pro Tyr Ser

<210> SEQ ID NO 5
<211> LENGTH: 54
<212> TYPE: DNA
<213> ORGANISM: Homo Sapiens
<220> FEATURE:
<221> NAME/KEY: CDS
<222> LOCATION: (1)...(54)

<400> SEQUENCE: 5 tat aac aag ttt aag aac atg ttc ttg gtt ggt gaa gga gat tcc gtg     48
Tyr Asn Lys Phe Lys Asn Met Phe Leu Val Gly Glu Gly Asp Ser Val
1               5                   10                  15 atc acc                                                              54
Ile Thr

<210> SEQ ID NO 6
<211> LENGTH: 18
<212> TYPE: PRT
<213> ORGANISM: Homo Sapiens
<220> FEATURE:
<221> NAME/KEY: PEPTIDE
<222> LOCATION: (1)...(18)

<400> SEQUENCE: 6

Tyr Asn Lys Phe Lys Asn Met Phe Leu Val Gly Glu Gly Asp Ser Val
1               5                   10                  15

Ile Thr

<210> SEQ ID NO 7
<211> LENGTH: 1017
<212> TYPE: DNA
<213> ORGANISM: Homo Sapiens
<220> FEATURE:
<221> NAME/KEY: CDS
<222> LOCATION: (1)...(1017)

<400> SEQUENCE: 7 aaa cca aga ggc aga ccc aaa atg gta aaa cag ccc tgt cct tca gag     48
Lys Pro Arg Gly Arg Pro Lys Met Val Lys Gln Pro Cys Pro Ser Glu
1               5                   10                  15 agt gac atc att act gaa gag gac aaa agt aag aaa aag ggg caa gag     96
Ser Asp Ile Ile Thr Glu Glu Asp Lys Ser Lys Lys Lys Gly Gln Glu
                20                  25                  30 gaa aaa caa cct aaa aag cag cct aag aag gat gaa gag ggc cag aag    144
Glu Lys Gln Pro Lys Lys Gln Pro Lys Lys Asp Glu Glu Gly Gln Lys
            35                  40                  45 gaa gaa gat aag cca aga aaa gag ccg gat aaa aaa gag ggg aag aaa    192
Glu Glu Asp Lys Pro Arg Lys Glu Pro Asp Lys Lys Glu Gly Lys Lys
        50                  55                  60 gaa gtt gaa tca aaa agg aaa aat tta gct aaa aca ggg gtt act tca    240
Glu Val Glu Ser Lys Arg Lys Asn Leu Ala Lys Thr Gly Val Thr Ser
65                  70                  75                  80 acc tcc gat tct gaa gaa gaa gga gat gat caa gaa ggt gaa aag aag    288
Thr Ser Asp Ser Glu Glu Glu Gly Asp Asp Gln Glu Gly Glu Lys Lys
                85                  90                  95
```

-continued

```
aga aaa ggt ggg agg aac ttt cag act gct cac aga agg aat atg ctg      336
Arg Lys Gly Gly Arg Asn Phe Gln Thr Ala His Arg Arg Asn Met Leu
        100                 105                 110 aaa ggc caa cat gag aaa gaa gca gca gat cga aaa cgc aag caa gag      384
Lys Gly Gln His Glu Lys Glu Ala Ala Asp Arg Lys Arg Lys Gln Glu
    115                 120                 125 gaa caa atg gaa act gag cag cag aat aaa gat gaa gga aag aag cca      432
Glu Gln Met Glu Thr Glu Gln Gln Asn Lys Asp Glu Gly Lys Lys Pro
130                 135                 140 gaa gtt aag aaa gtg gag aag aag cga gaa aca tca atg gat tct cga      480
Glu Val Lys Lys Val Glu Lys Lys Arg Glu Thr Ser Met Asp Ser Arg
145                 150                 155                 160 ctt caa agg ata cat gct gag att aaa aat tca ctc aaa att gat aat      528
Leu Gln Arg Ile His Ala Glu Ile Lys Asn Ser Leu Lys Ile Asp Asn
                165                 170                 175 ctt gat gtg aac aga tgc att gag gcc ttg gat gaa ctt gct tca ctt      576
Leu Asp Val Asn Arg Cys Ile Glu Ala Leu Asp Glu Leu Ala Ser Leu
            180                 185                 190 cag gtc aca atg caa caa gct cag aaa cac aca gag atg att act aca      624
Gln Val Thr Met Gln Gln Ala Gln Lys His Thr Glu Met Ile Thr Thr
        195                 200                 205 ctg aaa aaa ata cgg cga ttc aaa gtt agt cag gta atc atg gaa aag      672
Leu Lys Lys Ile Arg Arg Phe Lys Val Ser Gln Val Ile Met Glu Lys
    210                 215                 220 tct aca atg ttg tat aac aag ttt aag aac atg ttc ttg gtt ggt gaa      720
Ser Thr Met Leu Tyr Asn Lys Phe Lys Asn Met Phe Leu Val Gly Glu
225                 230                 235                 240 gga gat tcc gtg atc acc caa gtg ctg aat aaa tct ctt gct gaa caa      768
Gly Asp Ser Val Ile Thr Gln Val Leu Asn Lys Ser Leu Ala Glu Gln
                245                 250                 255 aga cag cat gag gaa gcg aat aaa acc aaa gat caa ggg aag aaa ggg      816
Arg Gln His Glu Glu Ala Asn Lys Thr Lys Asp Gln Gly Lys Lys Gly
            260                 265                 270 cca aac aaa aag cta gag aag gaa caa aca ggg tca aag act cta aat      864
Pro Asn Lys Lys Leu Glu Lys Glu Gln Thr Gly Ser Lys Thr Leu Asn
        275                 280                 285 gga gga tct gat gct caa gat ggt aat cag cca caa cat aac ggg gag      912
Gly Gly Ser Asp Ala Gln Asp Gly Asn Gln Pro Gln His Asn Gly Glu
    290                 295                 300 agc aat gaa gac agc aaa gac aac cat gaa gcc agc acg aag aaa aag      960
Ser Asn Glu Asp Ser Lys Asp Asn His Glu Ala Ser Thr Lys Lys Lys
305                 310                 315                 320 cca tcc agt gaa gag aga gag act gaa ata tct ctg aag gat tct aca     1008
Pro Ser Ser Glu Glu Arg Glu Thr Glu Ile Ser Leu Lys Asp Ser Thr
                325                 330                 335 cta gat aac                                                         1017
Leu Asp Asn
```

<210> SEQ ID NO 8
<211> LENGTH: 339
<212> TYPE: PRT
<213> ORGANISM: Homo Sapiens
<220> FEATURE:
<221> NAME/KEY: PEPTIDE
<222> LOCATION: (1)...(339)

<400> SEQUENCE: 8

```
Lys Pro Arg Gly Arg Pro Lys Met Val Lys Gln Pro Cys Pro Ser Glu
1               5                   10                  15

Ser Asp Ile Ile Thr Glu Glu Asp Lys Ser Lys Lys Gly Gln Glu
            20                  25                  30
```

```
Glu Lys Gln Pro Lys Lys Gln Pro Lys Lys Asp Glu Glu Gly Gln Lys
            35                  40                  45

Glu Glu Asp Lys Pro Arg Lys Glu Pro Asp Lys Lys Glu Gly Lys Lys
 50                  55                  60

Glu Val Glu Ser Lys Arg Lys Asn Leu Ala Lys Thr Gly Val Thr Ser
 65                  70                  75                  80

Thr Ser Asp Ser Glu Glu Gly Asp Gln Glu Gly Glu Lys Lys
                85                  90                  95

Arg Lys Gly Gly Arg Asn Phe Gln Thr Ala His Arg Arg Asn Met Leu
                100                 105                 110

Lys Gly Gln His Glu Lys Glu Ala Ala Asp Arg Lys Arg Lys Gln Glu
                115                 120                 125

Glu Gln Met Glu Thr Glu Gln Gln Asn Lys Asp Glu Gly Lys Lys Pro
                130                 135                 140

Glu Val Lys Lys Val Glu Lys Lys Arg Glu Thr Ser Met Asp Ser Arg
145                 150                 155                 160

Leu Gln Arg Ile His Ala Glu Ile Lys Asn Ser Leu Lys Ile Asp Asn
                165                 170                 175

Leu Asp Val Asn Arg Cys Ile Glu Ala Leu Asp Glu Leu Ala Ser Leu
                180                 185                 190

Gln Val Thr Met Gln Gln Ala Gln Lys His Thr Glu Met Ile Thr Thr
                195                 200                 205

Leu Lys Lys Ile Arg Arg Phe Lys Val Ser Gln Val Ile Met Glu Lys
                210                 215                 220

Ser Thr Met Leu Tyr Asn Lys Phe Lys Asn Met Phe Leu Val Gly Glu
225                 230                 235                 240

Gly Asp Ser Val Ile Thr Gln Val Leu Asn Lys Ser Leu Ala Glu Gln
                245                 250                 255

Arg Gln His Glu Glu Ala Asn Lys Thr Lys Asp Gln Gly Lys Lys Gly
                260                 265                 270

Pro Asn Lys Lys Leu Glu Lys Glu Gln Thr Gly Ser Lys Thr Leu Asn
                275                 280                 285

Gly Gly Ser Asp Ala Gln Asp Gly Asn Gln Pro Gln His Asn Gly Glu
                290                 295                 300

Ser Asn Glu Asp Ser Lys Asp Asn His Glu Ala Ser Thr Lys Lys Lys
305                 310                 315                 320

Pro Ser Ser Glu Glu Arg Glu Thr Glu Ile Ser Leu Lys Asp Ser Thr
                325                 330                 335

Leu Asp Asn

<210> SEQ ID NO 9
<211> LENGTH: 13
<212> TYPE: PRT
<213> ORGANISM: Homo Sapiens
<220> FEATURE:
<221> NAME/KEY: PEPTIDE
<222> LOCATION: (1)...(13)

<400> SEQUENCE: 9

Phe Ala Lys Met Lys Gly Tyr Pro His Trp Pro Ala Arg
1               5                   10

<210> SEQ ID NO 10
<211> LENGTH: 15
<212> TYPE: PRT
<213> ORGANISM: Homo Sapiens
```

```
<220> FEATURE:
<221> NAME/KEY: PEPTIDE
<222> LOCATION: (1)...(15)

<400> SEQUENCE: 10

Phe Phe Phe Gly Thr His Glu Thr Ala Phe Leu Gly Pro Lys Asp
1               5                   10                  15

<210> SEQ ID NO 11
<211> LENGTH: 9
<212> TYPE: PRT
<213> ORGANISM: Homo Sapiens
<220> FEATURE:
<221> NAME/KEY: PEPTIDE
<222> LOCATION: (1)...(9)

<400> SEQUENCE: 11

Gly Lys Pro Asn Lys Arg Lys Gly Phe
1               5

<210> SEQ ID NO 12
<211> LENGTH: 6
<212> TYPE: PRT
<213> ORGANISM: Homo Sapiens
<220> FEATURE:
<221> NAME/KEY: PEPTIDE
<222> LOCATION: (1)...(6)

<400> SEQUENCE: 12

Glu Gly Leu Trp Glu Ile
1               5

<210> SEQ ID NO 13
<211> LENGTH: 1586
<212> TYPE: DNA
<213> ORGANISM: Homo Sapiens

<400> SEQUENCE: 13
atgactcgcg atttcaaacc tggagacctc atcttcgcca agatgaaagg ttatccccat      60
tggccagctc gagtagacga agttcctgat ggagctgtaa agccaccac aaacaaacta     120 cccatttttct tttttggaac tcatgagact gctttttag gaccaaagga tatatttcct    180
tactcagaaa ataaggaaaa gtatggcaaa ccaaataaaa gaaaaggttt taatgaaggt     240
ttatgggaga tagataacaa tccaaaagtg aaattttcaa gtcaacaggc agcaactaaa     300
caatcaaatg catcatctga tgttgaagtt gaagaaaagg aaactagtgt ttcaaaggaa     360
gataccgacc atgaagaaaa agccagcaat gaggatgtga ctaaagcagt tgacataact     420
actccaaaag ctgccagaag ggggagaaag agaaaggcag aaaacaagt agaaactgag      480 gaggcaggag tagtgacaac agcaacagca tctgttaatc taaaagtgag tcctaaaaga     540
ggacgacctg cagctacaga agtcaagatt ccaaaaccaa gaggcagacc caaaatggta     600
aaacagccct gtccttcaga gagtgacatc attactgaag aggacaaaag taagaaaaag     660
gggcaagagg aaaaacaacc taaaaagcag cctaagaagg atgaagaggg ccagaaggaa     720
gaagataagc caagaaaaga gccggataaa aagaggggga gaaagaagt tgaatcaaaa     780 aggaaaaatt tagctaaaac agggggttact tcaacctccg attctgaaga agaaggagat     840
gatcaagaag gtgaaaagaa gagaaaaggt gggaggaact ttcagactgc tcacagaagg     900
aatatgctga aggccaaca tgagaaagaa gcagcagatc gaaaacgcaa gcaagaggaa     960
caaatggaaa ctgagcagca gaataaagat gaaggaaaga agccagaagt taagaaagtg    1020
```

```
gagaagaagc gagaaacatc aatggattct cgacttcaaa ggatacatgc tgagattaaa    1080
aattcactca aaattgataa tcttgatgtg aacagatgca ttgaggcctt ggatgaactt    1140
gcttcacttc aggtcacaat gcaacaagct cagaaacaca cagagatgat tactacactg    1200
aaaaaaatac ggcgattcaa agttagtcag gtaatcatgg aaaagtctac aatgttgtat    1260
aacaagttta agaacatgtt cttggttggt gaaggagatt ccgtgatcac ccaagtgctg    1320
aataaatctc ttgctgaaca agacagcat gaggaagcga ataaaaccaa agatcaaggg    1380
aagaaagggc caaacaaaaa gctagagaag gaacaaacag ggtcaaagac tctaaatgga    1440
ggatctgatg ctcaagatgg taatcagcca caacataacg gggagagcaa tgaagacagc    1500
aaagacaacc atgaagccag cacgaagaaa aagccatcca gtgaagagag agagactgaa    1560
atatctctga aggattctac actaga                                         1586
```

<210> SEQ ID NO 14
<211> LENGTH: 240
<212> TYPE: PRT
<213> ORGANISM: Homo Sapiens

<400> SEQUENCE: 14

```
Met Ser Arg Ser Asn Arg Gln Lys Glu Tyr Lys Cys Gly Asp Leu Val
1               5                   10                  15
Phe Ala Lys Met Lys Gly Tyr Pro His Trp Pro Ala Arg Ile Asp Glu
            20                  25                  30
Met Pro Glu Ala Ala Val Lys Ser Thr Ala Asn Lys Tyr Gln Val Phe
        35                  40                  45
Phe Phe Gly Thr His Glu Thr Ala Phe Leu Gly Pro Lys Asp Leu Phe
    50                  55                  60
Pro Tyr Glu Glu Ser Lys Glu Lys Phe Gly Lys Pro Asn Lys Arg Lys
65                  70                  75                  80
Gly Phe Ser Glu Gly Leu Trp Glu Ile Glu Asn Asn Pro Thr Val Lys
                85                  90                  95
Ala Ser Gly Tyr Gln Ser Ser Gln Lys Lys Ser Cys Val Glu Pro
            100                 105                 110
Glu Pro Glu Pro Glu Ala Ala Glu Gly Asp Gly Asp Lys Lys Gly Asn
        115                 120                 125
Ala Glu Gly Ser Ser Asp Glu Glu Gly Lys Leu Val Ile Asp Glu Pro
    130                 135                 140
Ala Lys Glu Lys Asn Glu Lys Gly Ala Leu Lys Arg Arg Ala Gly Asp
145                 150                 155                 160
Leu Leu Glu Asp Ser Pro Lys Arg Pro Lys Glu Ala Glu Asn Pro Glu
                165                 170                 175
Gly Glu Glu Lys Glu Ala Ala Thr Leu Glu Val Glu Arg Pro Leu Pro
            180                 185                 190
Met Glu Val Glu Lys Asn Ser Thr Pro Ser Glu Pro Gly Ser Gly Arg
        195                 200                 205
Gly Pro Pro Gln Glu Glu Glu Glu Glu Asp Glu Glu Glu Ala
    210                 215                 220
Thr Lys Glu Asp Ala Glu Ala Pro Gly Ile Arg Asp His Glu Ser Leu
225                 230                 235                 240
```

<210> SEQ ID NO 15
<211> LENGTH: 237
<212> TYPE: PRT
<213> ORGANISM: Mus Musculus

```
<400> SEQUENCE: 15

Met Ser Arg Ser Asn Arg Gln Lys Glu Tyr Lys Cys Gly Asp Leu Val
1               5                   10                  15

Phe Ala Lys Met Lys Gly Tyr Pro His Trp Pro Ala Arg Ile Asp Glu
            20                  25                  30

Met Pro Glu Ala Ala Val Lys Ser Thr Ala Asn Lys Tyr Gln Val Phe
        35                  40                  45

Phe Phe Gly Thr His Glu Thr Ala Phe Leu Gly Pro Lys Asp Leu Phe
    50                  55                  60

Pro Tyr Glu Glu Ser Lys Glu Lys Phe Gly Lys Pro Asn Lys Arg Lys
65                  70                  75                  80

Gly Phe Ser Glu Gly Leu Trp Glu Ile Glu Asn Asn Pro Thr Val Lys
                85                  90                  95

Ala Ser Gly Tyr Gln Ser Ser Gln Lys Lys Ser Cys Ala Ala Glu Pro
            100                 105                 110

Glu Val Glu Pro Glu Ala His Glu Gly Asp Gly Asp Lys Lys Gly Ser
        115                 120                 125

Ala Glu Gly Ser Ser Asp Glu Gly Lys Leu Val Ile Asp Glu Pro
    130                 135                 140

Ala Lys Glu Lys Asn Glu Lys Gly Thr Leu Lys Arg Arg Ala Gly Asp
145                 150                 155                 160

Val Leu Glu Asp Ser Pro Lys Arg Pro Lys Glu Ser Gly Asp His Glu
                165                 170                 175

Glu Glu Asp Lys Glu Ile Ala Ala Leu Glu Gly Glu Arg His Leu Pro
            180                 185                 190

Val Glu Val Glu Lys Asn Ser Thr Pro Ser Glu Pro Asp Ser Gly Gln
        195                 200                 205

Gly Pro Pro Ala Glu Glu Glu Gly Glu Glu Ala Ala Lys Glu
    210                 215                 220

Glu Ala Glu Ala Pro Gly Val Arg Asp His Glu Ser Leu
225                 230                 235

<210> SEQ ID NO 16
<211> LENGTH: 510
<212> TYPE: PRT
<213> ORGANISM: Homo Sapiens

<400> SEQUENCE: 16

Lys Glu Leu Glu Arg Leu Ser Pro Glu Glu Ala Ala His Gln Lys Ala
1               5                   10                  15

Val Val Glu Arg Leu Leu Gln Glu Asp Pro Trp His Val Ala Lys Leu
            20                  25                  30

Val Lys Ser Tyr Leu Gln Gln His Asn Ile Pro Gln Arg Glu Val Val
        35                  40                  45

Asp Thr Thr Gly Leu Asn Gln Ser His Leu Ser Gln His Leu Asn Lys
    50                  55                  60

Gly Thr Pro Met Lys Thr Gln Lys Arg Ala Ala Leu Tyr Ala Trp Tyr
65                  70                  75                  80

Val Gly Lys Gln Arg Glu Ile Ala Arg Gln Phe Thr His Ala Gly His
                85                  90                  95

Ser Met Ile Thr Asp Asp Met Ser Cys Asp Val Pro Asn Lys Lys
            100                 105                 110

Met Arg Arg Asn Arg Phe Lys Trp Gly Pro Ala Ser Gln Gln Ile Leu
        115                 120                 125
```

```
Phe Gln Ala Tyr Glu Arg Gln Lys Asn Pro Ser Lys Glu Glu Arg Glu
    130                 135                 140
Ala Leu Val Glu Glu Cys Asn Arg Ala Glu Cys Leu Gln Arg Gly Val
145                 150                 155                 160
Ser Pro Ser Gln Ala Gln Gly Leu Gly Ser Asn Leu Val Thr Glu Val
                165                 170                 175
Arg Val Tyr Asn Trp Phe Ala Asn Ser Gly Lys Glu Glu Ala Phe Arg
            180                 185                 190
His Lys Leu Ala Met Asp Thr Tyr Asn Gly Gln Gln Ser Ser Ala Gln
        195                 200                 205
Pro Leu Ser Thr His Asp Leu Pro His Gly Lys Thr Pro Gly Phe Arg
    210                 215                 220
Tyr Thr Gln Asp Ser Ser Thr Asp Arg Ser Ala Ala Met Ala Asn Ser
225                 230                 235                 240
Gln Ser Thr Leu Ser Pro Ser Ala Leu Glu Pro Ser His Ile Leu Met
                245                 250                 255
Asn Ser Asp Ser Lys Met Val Pro Val Ser Gly Gly Ser Leu Pro Pro
            260                 265                 270
Val Cys Thr Leu Thr Ala Leu His Ser Leu Asp His Ser Gln His Thr
        275                 280                 285
Leu Gly Gln Thr Gln Asn Leu Ile Met Ala Ser Leu Pro Ser Val Met
    290                 295                 300
Thr Ile Gly Thr Asp Ser Ala Leu Gly Pro Ala Phe Ser Asn Pro Gly
305                 310                 315                 320
Ser Ser Thr Leu Val Ile Gly Leu Ala Ser Gln Thr Gln Ser Val Pro
                325                 330                 335
Val Ile Asn Ser Val Gly Ser Ser Leu Thr Thr Leu Gln Ser Val Gln
            340                 345                 350
Phe Ser Gln Gln Leu His Pro Ser His Gln Gln Pro Ile Val Gln Gln
        355                 360                 365
Val Gln Ser His Met Ala Gln Ser Pro Phe Met Ala Thr Met Ala Gln
    370                 375                 380
Leu Gln Ser Pro His Ala Leu Tyr Ser His Lys Pro Glu Val Ala Gln
385                 390                 395                 400
Tyr Thr Ser Ala Gly Phe Phe Pro Gln Thr Met Val Ile Thr Asp Thr
                405                 410                 415
Ser Asn Leu Gly Thr Leu Thr Ser Leu Thr Pro Ser Lys Gln Val Val
            420                 425                 430
Ser His His Pro Thr Ala His Gly Asp Ser Pro Gly Ser Gln Leu His
        435                 440                 445
Asn Gln Asp Ser Ser Ile Leu His Leu His Pro Ser His Arg Leu Ser
    450                 455                 460
Pro Ile Pro Thr Val Ser Ser Ala Ser Leu Ile His Tyr His Asn Ser
465                 470                 475                 480
Ser Ser Pro Glu Asn His Ser His Leu Leu Ser Pro Ser His Asn Thr
                485                 490                 495
Ile Asp Ser Phe Ile Ser Thr Gln Met Ala Ser Ser Ser Gln
            500                 505                 510

<210> SEQ ID NO 17
<211> LENGTH: 310
<212> TYPE: DNA
<213> ORGANISM: Homo Sapiens
<220> FEATURE:
<221> NAME/KEY: 5'UTR
```

<222> LOCATION: (1)...(310)

<400> SEQUENCE: 17

```
gggagccgcg cgggagcagc gcagctacgg cggcggcagc ggcggcgcgg ttgcgattcc      60
gagccgttga gacgcctctg cggcagctgg tggcgcaggt ggcttgcgtg gacgcgggta     120
gaggcgaccg gccagcaacc gcagcgtcgg cgcccgcggc cccggcagca ggcgcgtcgg     180
gacgccccga ggcatcctcc cccgcccgcg ggcccggtag ctgggcccgc gtccgccgcc     240
cgcatccccg cgccgccgca tctcctcgcc gcctcccggg cttcggaccc ccggtctcgc     300
ccccggaaac                                                            310
```

<210> SEQ ID NO 18
<211> LENGTH: 1461
<212> TYPE: DNA
<213> ORGANISM: Homo Sapiens
<220> FEATURE:
<221> NAME/KEY: 3'UTR
<222> LOCATION: (1)...(1461)

<400> SEQUENCE: 18

```
ctaggttgac atacctggaa tatagagaac acttgagaag tttgtaatgg ttttcatttg      60
aaatagactg ctggaagttt aaattttat aagcataggt ttgatgttga aaacttgttt     120
tgagggagaa atccctttg ttttaaagta agtaaacat tatcgctaag tgtaacttgt     180
gcagtattaa cagctacatt atacagtaaa tgtgggataa atccattta gaaaatgtta     240
aactgctttt ccagacatgg ttgtagcata ttttcaatta gtgtgtgtat gttaatgtgt     300
aattgatagt agaacaaagt tacatttta aaactgctac ttgtataaac cttgcctctt     360
ttcccaaata ctgtgggttt tgtgcatagt ttttacaaac cttggattta ccagactgtc     420
ttttcactgt ttgtgggttt tgtagaagtt acacatttt atggtagata aaatgttact     480
tctatacaag tactcactcc cttttatca aaagttaatt ttaatctcac agtctacatt     540
gtgctacatt atccagcttc tttggaacaa tgtgtgctct gtatggtttt ttttggtatg     600
acaactaatt aagcaactga cattgaactg agaattctac aaactataaa acattaattt     660
ttgaaggtaa tttagttttg tggctgggca ttcagtgaag tcttaggact tctttgcaga     720
caactgactg ggtatatata ggaatgaatc tggctttagg gttaaatcat ttaaggtcct     780
tttataggca ggcactagta actaaaactg aaaactaagt aagtttattt ttgaggaatg     840
ttgttaaaaa tgtctttagg aagtcactaa aacttaattg gaagaaaaaa tcatgatgct     900
tatacaataa atatgaataa atgttatata aggaaactca cctatttgaa atcatggcta     960
tattgttttt atttctaga ttccaaaaat acaaacacta gttgttccag cattgtactt    1020
tgataagtct gtacattgac gtgtatggac taaatccagg gtaaaatcaa tgttacaaaa    1080
tttaagggta tgttaactaa aggatagcat ttctaagata ttttgaatat tagggtcatt    1140
tggcacttct cagcaagtag gatacttctc atgtttttga aattatatga atatggaaaa    1200
aaatggctta agaccagcgt ctctgtatga cattgtgtgg ttgaccctct gagataactg    1260
ttttcatcta cagaattgca ttttttgcttt taaagaggtc ttataatgga actaggaatc    1320
accgttttga gagaacctgc atatatacca gtcattatct gtttggtcct tatacagtttt   1380
taacttactt agatttattc tagttaagcc ataagttcaa cgtgtaaact tgttttcatt    1440
aaagaatttt tctatcaaaa a                                              1461
```

<210> SEQ ID NO 19

<211> LENGTH: 31
<212> TYPE: DNA
<213> ORGANISM: Homo Sapiens

<400> SEQUENCE: 19
ccccggatcc atgactcgcg atttcaaacc t                                      31

<210> SEQ ID NO 20
<211> LENGTH: 31
<212> TYPE: DNA
<213> ORGANISM: Homo Sapiens

<400> SEQUENCE: 20
tcttgaattc tgtagctgca ggtcgtcctc t                                      31

<210> SEQ ID NO 21
<211> LENGTH: 2525
<212> TYPE: DNA
<213> ORGANISM: Homo Sapiens
<300> PUBLICATION INFORMATION:
<308> DATABASE ACCESSION NUMBER: U94319
<309> DATABASE ENTRY DATE: 1997-04-21

<400> SEQUENCE: 21

| | | | | |
|---|---|---|---|---|
| agaggacgac | ctgcagctac | agaagtcaag | attccaaaac caagaggcag acccaaaatg | 60 |
| gtaaaacagc | cctgtccttc | agagagtgac | atcattactg aagaggacaa agtaagaaa | 120 |
| aagggcaag | aggaaaaaca | acctaaaaag | cagcctaaga aggatgaaga gggccagaag | 180 |
| gaagaagata | agccaagaaa | agagccggat | aaaaagagg ggaagaaaga agttgaatca | 240 |
| aaaaggaaaa | atttagctaa | aacagggtt | acttcaccct ccgattctga agaagaagga | 300 |
| gatgatcaag | aaggtgaaaa | gaagagaaaa | ggtgggagga actttcagac tgctcacaga | 360 |
| aggaatatgc | tgaaaggcca | acatgagaaa | gaagcagcag atcgaaaacg caagcaagag | 420 |
| gaacaaatgg | aaactgagca | gcagaataaa | gatgaaggaa agaagccaga agttaagaaa | 480 |
| gtggagaaga | agcgagaaac | atcaatggat | tctcgacttc aaaggataca tgctgagatt | 540 |
| aaaaattcac | tcaaaattga | taatcttgat | gtgaacagat gcattgaggc cttggatgaa | 600 |
| cttgcttcac | ttcaggtcac | aatgcaacaa | gctcagaaac acacagagat gattactaca | 660 |
| ctgaaaaaaa | tacggcgatt | caaagttagt | caggtaatca tggaaaagtc tacaatgttg | 720 |
| tttaacaagt | ttaagaacat | gttcttggtt | ggtgaaggag attccgtgat cacccaagtg | 780 |
| ctgaataaat | ctcttgctga | acaaagacag | catgaggaag cgaataaaac caaagatcaa | 840 |
| gggaagaaag | ggccaaacaa | aaagctagag | aaggaacaaa caggggtcaaa gactctaaat | 900 |
| ggaggatctg | atgctcaaga | tggtaatcag | ccacaacata acgggagag caatgaagac | 960 |
| agcaaagaca | accatgaagc | cagcacgaag | aaaaagccat ccagtgaaga gagagagact | 1020 |
| gaaatatctc | tgaaggattc | tacactagat | aactaggttg acatacctgg aatatagaga | 1080 |
| acacttgaga | agtttgtaat | ggttttcatt | tgaaatagac tgctgaaagt tttaaatttt | 1140 |
| tataagcata | ggtttgatgt | tgaaaacttg | ttttgaggga gaaatccct ttgttttaaa | 1200 |
| gtaaagtaaa | cattatcgct | aagtgtactt | gtgcagtatt aacagctaca ttatacagta | 1260 |
| aatgtgggat | ggaatccatt | taggaaatgt | taaactgctt ttccagacat ggttgtagca | 1320 |
| tattttcaat | tagtgtgtgt | atgttaatgt | gtaattgata gtagaacaaa gttacatttt | 1380 |
| taaaactgct | acttgtataa | accttgcctc | ttttcccaaa tactgtgggt tttgtgcata | 1440 |
| gtttttacaa | accttggatt | taccagactg | tcttttcact gtttgtgggt tttgtagaag | 1500 |

-continued

```
ttacacattt ttatggtaga taaaatgtta cttctataca agtactcact ccctttttat    1560
caaaagttaa ttttaatctc acagtctaca ttgtgctaca ttatccagct tctttggaac    1620
aatgtgtgct ctgtatggtt ttttttggta tgacaactaa ttaagcaact gacattgaac    1680
tgagaattct acaaactata aaacattaat ttttgaaggt aatttagttt tgtggctggg    1740
cattcagtga agtcttagga cttctttgca gacaactgac tgggtatata taggaatgaa    1800
tctggcttta gggttaaatc atttaaggtc cttttatagg caggcactag taactaaaac    1860
tgaaaactaa gtaagtttat ttttgaggaa tgttgttaaa aatgtcttta ggaagtcact    1920
aaaacttaat tggaagaaaa aatcatgatg cttatacaat aaatatgaat aaatgttata    1980
taaggaaact cacctatttg aaatcatggc tatattgttt ttattttcta gattcccaca    2040
aatacacaca ctagttgttc cagcattgta ctttgataag tctgtacatt gacgtgtatg    2100
gactaaatcc agggtaaaat caatgttaca aaatttaagg gtatgttaac taaaggatag    2160
catttctaag atattttgaa tattagggtc atttggcact tctcagcaag taggatactt    2220
ctcatgtttt gaaattatat gaatatgaaa aaaatggct taagaccagc gtctctgtat    2280
gacattgtgt ggtgaccctc tgagataact gttttcatct acagaattgc attttttgctt    2340 ttaaagaggt cttataatgg aactaggaat caccgttttg agaggacctg catatatacc    2400
agtcattatc tgtttggtcc ttatacagtt ttaacttact tagattttatt ctagttaagc    2460 cataagttcc acgtgtaaac ttgttttcat taaagaattt ttctatcaaa aaaaaaaaa    2520 aaaaa                                                                 2525
```

<210> SEQ ID NO 22
<211> LENGTH: 351
<212> TYPE: PRT
<213> ORGANISM: Homo Sapiens

<400> SEQUENCE: 22

```
Arg Gly Arg Pro Ala Ala Thr Glu Val Lys Ile Pro Lys Pro Arg Gly
1               5                   10                  15

Arg Pro Lys Met Val Lys Gln Pro Cys Pro Ser Glu Ser Asp Ile Ile
            20                  25                  30

Thr Glu Glu Asp Lys Ser Lys Lys Lys Gly Gln Glu Glu Lys Gln Pro
        35                  40                  45

Lys Lys Gln Pro Lys Lys Asp Glu Glu Gly Gln Lys Glu Glu Asp Lys
    50                  55                  60

Pro Arg Lys Glu Pro Asp Lys Lys Glu Gly Lys Lys Glu Val Glu Ser
65                  70                  75                  80

Lys Arg Lys Asn Leu Ala Lys Thr Gly Val Thr Ser Pro Ser Asp Ser
                85                  90                  95

Glu Glu Glu Gly Asp Asp Gln Glu Gly Glu Lys Lys Arg Lys Gly Gly
            100                 105                 110

Arg Asn Phe Gln Thr Ala His Arg Arg Asn Met Leu Lys Gly Gln His
        115                 120                 125

Glu Lys Glu Ala Ala Asp Arg Lys Arg Lys Gln Glu Gln Met Glu
    130                 135                 140

Thr Glu Gln Gln Asn Lys Asp Glu Gly Lys Lys Pro Glu Val Lys Lys
145                 150                 155                 160

Val Glu Lys Lys Arg Glu Thr Ser Met Asp Ser Arg Leu Gln Arg Ile
                165                 170                 175

His Ala Glu Ile Lys Asn Ser Leu Lys Ile Asp Asn Leu Asp Val Asn
            180                 185                 190
```

-continued

```
Arg Cys Ile Glu Ala Leu Asp Glu Leu Ala Ser Leu Gln Val Thr Met
    195                 200                 205
Gln Gln Ala Gln Lys His Thr Glu Met Ile Thr Thr Leu Lys Lys Ile
    210                 215                 220
Arg Arg Phe Lys Val Ser Gln Val Ile Met Glu Lys Ser Thr Met Leu
225                 230                 235                 240
Phe Asn Lys Phe Lys Asn Met Phe Leu Val Gly Glu Gly Asp Ser Val
            245                 250                 255
Ile Thr Gln Val Leu Asn Lys Ser Leu Ala Glu Gln Arg Gln His Glu
            260                 265                 270
Glu Ala Asn Lys Thr Lys Asp Gln Gly Lys Lys Gly Pro Asn Lys Lys
            275                 280                 285
Leu Glu Lys Glu Gln Thr Gly Ser Lys Thr Leu Asn Gly Gly Ser Asp
    290                 295                 300
Ala Gln Asp Gly Asn Gln Pro Gln His Asn Gly Glu Ser Asn Glu Asp
305                 310                 315                 320
Ser Lys Asp Asn His Glu Ala Ser Thr Lys Lys Lys Pro Ser Ser Glu
            325                 330                 335
Glu Arg Glu Thr Glu Ile Ser Leu Lys Asp Ser Thr Leu Asp Asn
                340                 345                 350
```